(12) United States Patent
Rouse et al.

(10) Patent No.: US 8,592,475 B2
(45) Date of Patent: Nov. 26, 2013

(54) INHIBITORS OF AKT ACTIVITY

(75) Inventors: Meagan B. Rouse, Collegeville, PA (US); Mark Andrew Seefeld, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 254 days.

(21) Appl. No.: 13/124,180

(22) PCT Filed: Oct. 14, 2009

(86) PCT No.: PCT/US2009/060618
§ 371 (c)(1),
(2), (4) Date: Apr. 14, 2011

(87) PCT Pub. No.: WO2010/045309
PCT Pub. Date: Apr. 22, 2010

(65) Prior Publication Data
US 2011/0196009 A1    Aug. 11, 2011

Related U.S. Application Data

(60) Provisional application No. 61/105,867, filed on Oct. 16, 2008, provisional application No. 61/150,410, filed on Feb. 6, 2009.

(51) Int. Cl.
| | |
|---|---|
| *A01N 43/56* | (2006.01) |
| *A61K 31/415* | (2006.01) |
| *C07D 231/00* | (2006.01) |
| *C07D 403/00* | (2006.01) |
| *C07D 403/02* | (2006.01) |
| *C07D 231/10* | (2006.01) |
| *C07D 231/12* | (2006.01) |

(52) U.S. Cl.
USPC ............... 514/406; 548/364.1; 548/365.7; 548/373.1

(58) Field of Classification Search
USPC ............ 514/406; 548/364.1, 365.7, 373.1
See application file for complete search history.

(56) References Cited

FOREIGN PATENT DOCUMENTS

| WO | WO 2005/113762 | 12/2005 |
| WO | WO 2008/098105 | 8/2008 |

*Primary Examiner* — Samira Jean-Louis
(74) *Attorney, Agent, or Firm* — Wayne J. Dustman; Edward R. Gimmi

(57) ABSTRACT

Invented are novel heterocyclic carboxamide compounds, the use of such compounds as inhibitors of protein kinase B activity and in the treatment of cancer and arthritis.

18 Claims, No Drawings

INHIBITORS OF AKT ACTIVITY

This application is a 371 of International Application No. PCT/US2009/060618, filed 14 Oct. 2009, which claims priority from U.S. Provisional Application 61/105,867, filed 16 Oct. 2008, and No. 61/150,410, filed 6 Feb. 2009, which are incorporated herein in their entirety.

FIELD OF THE INVENTION

This invention relates to novel heterocyclic carboxamide compounds, the use of such compounds as inhibitors of protein kinase B (hereinafter PKB/Akt, PKB or Akt) activity and in the treatment of cancer and arthritis.

BACKGROUND OF THE INVENTION

The present invention relates to heterocyclic carboxamide containing compounds that are inhibitors of the activity of one or more of the isoforms of the serine/threonine kinase, Akt (also known as protein kinase B), suitably the compounds of the invention are inhibitors of the activity of all three isoforms of the serine/threonine kinase, Akt. The present invention also relates to pharmaceutical compositions comprising such compounds and methods of using the instant compounds in the treatment of cancer and arthritis (Liu et al. *Current Opin. Pharmacology* 3:317-22 (2003)).

Apoptosis (programmed cell death) plays essential roles in embryonic development and pathogenesis of various diseases, such as degenerative neuronal diseases, cardiovascular diseases and cancer. Recent work has led to the identification of various pro- and anti-apoptotic gene products that are involved in the regulation or execution of programmed cell death. Expression of anti-apoptotic genes, such as Bcl2 or Bcl-$x_L$, inhibits apoptotic cell death induced by various stimuli. On the other hand, expression of pro-apoptotic genes, such as Bax or Bad, leads to programmed cell death (Adams et al. *Science*, 281:1322-1326 (1998)). The execution of programmed cell death is mediated by caspase-1 related proteinases, including caspase-3, caspase-7, caspase-8 and caspase-9 etc (Thornberry et al. *Science*, 281:1312-1316 (1998)).

The phosphatidylinositol 3'-OH kinase (PI3K)/Akt/PKB pathway appears important for regulating cell survival/cell death (Kulik et al. *Mol. Cell. Biol.* 17:1595-1606 (1997); Franke et al, *Cell*, 88:435-437 (1997); Kauffmann-Zeh et al. *Nature* 385:544-548 (1997) Hemmings *Science*, 275:628-630 (1997); Dudek et al., *Science*, 275:661-665 (1997)). Survival factors, such as platelet derived growth factor (PDGF), nerve growth factor (NGF) and insulin-like growth factor-1 (IGF-I), promote cell survival under various conditions by inducing the activity of PI3K (Kulik et al. 1997, Hemmings 1997). Activated PI3K leads to the production of phosphatidylinositol (3,4,5)-triphosphate (PtdIns (3,4,5)-P3), which in turn binds to, and promotes the activation of, the serine/threonine kinase Akt, which contains a pleckstrin homology (PH)-domain (Franke et al *Cell*, 81:727-736 (1995); Hemmings *Science*, 277:534 (1997); Downward, *Curr. Opin. Cell Biol.* 10:262-267 (1998), Alessi et al., *EMBO J.* 15: 6541-6551 (1996)). Specific inhibitors of PI3K or dominant negative Akt/PKB mutants abolish survival-promoting activities of these growth factors or cytokines. It has been previously disclosed that inhibitors of PI3K (LY294002 or wortmannin) blocked the activation of Akt/PKB by upstream kinases. In addition, introduction of constitutively active PI3K or Akt/PKB mutants promotes cell survival under conditions in which cells normally undergo apoptotic cell death (Kulik et al. 1997, Dudek et al. 1997).

Analysis of Akt levels in human tumors showed that Akt2 is overexpressed in a significant number of ovarian (J. Q. Cheung et al. *Proc. Natl. Acad. Sci. U.S.A.* 89:9267-9271 (1992)) and pancreatic cancers (J. Q. Cheung et al. *Proc. Natl. Acad. Sci. U.S.A.* 93:3636-3641 (1996)). Similarly, Akt3 was found to be overexpressed in breast and prostate cancer cell lines (Nakatani et al. *J. Biol. Chem.* 274:21528-21532 (1999). It was demonstrated that Akt-2 was over-expressed in 12% of ovarian carcinomas and that amplification of Akt was especially frequent in 50% of undifferentiated tumors, suggestion that Akt may also be associated with tumor aggressiveness (Bellacosa, et al., *Int. J. Cancer*, 64, pp. 280-285, 1995). Increased Akt1 kinase activity has been reported in breast, ovarian and prostate cancers (Sun et al. *Am. J. Pathol.* 159: 431-7 (2001)).

The tumor suppressor PTEN, a protein and lipid phosphatase that specifically removes the 3' phosphate of PtdIns (3,4,5)-P3, is a negative regulator of the PI3K/Akt pathway (Li et al. *Science* 275:1943-1947 (1997), Stambolic et al. *Cell* 95:29-39 (1998), Sun et al. *Proc. Natl. Acad. Sci. U.S.A.* 96:6199-6204 (1999)). Germline mutations of PTEN are responsible for human cancer syndromes such as Cowden disease (Liaw et al. *Nature Genetics* 16:64-67 (1997)). PTEN is deleted in a large percentage of human tumors and tumor cell lines without functional PTEN show elevated levels of activated Akt (Li et al. supra, Guldberg et al. *Cancer Research* 57:3660-3663 (1997), Risinger et al. *Cancer Research* 57:4736-4738 (1997)).

These observations demonstrate that the PI3K/Akt pathway plays important roles for regulating cell survival or apoptosis in tumorigenesis.

Three members of the Akt/PKB subfamily of second-messenger regulated serine/threonine protein kinases have been identified and termed Akt1/PKBα, Akt2/PKBβ, and Akt3/PKBγ respectively. The isoforms are homologous, particularly in regions encoding the catalytic domains. Akt/PKBs are activated by phosphorylation events occurring in response to PI3K signaling. PI3K phosphorylates membrane inositol phospholipids, generating the second messengers phosphatidyl-inositol 3,4,5-trisphosphate and phosphatidylinositol 3,4-bisphosphate, which have been shown to bind to the PH domain of Akt/PKB. The current model of Akt/PKB activation proposes recruitment of the enzyme to the membrane by 3'-phosphorylated phosphoinositides, where phosphorylation of the regulatory sites of Akt/PKB by the upstream kinases occurs (B. A. Hemmings, *Science* 275:628-630 (1997); B. A. Hemmings, *Science* 276:534 (1997); J. Downward, *Science* 279:673-674 (1998)).

Phosphorylation of Akt1/PKBα occurs on two regulatory sites, Thr$^{308}$ in the catalytic domain activation loop and on Ser$^{473}$ near the carboxy terminus (D. R. Alessi et al. *EMBO J.* 15:6541-6551 (1996) and R. Meier et al. *J. Biol. Chem.* 272: 30491-30497 (1997)). Equivalent regulatory phosphorylation sites occur in Akt2/PKBβ and Akt3/PKBγ. The upstream kinase, which phosphorylates Akt/PKB at the activation loop site has been cloned and termed 3'-phosphoinositide dependent protein kinase 1 (PDK1). PDK1 phosphorylates not only Akt/PKB, but also p70 ribosomal S6 kinase, p90RSK, serum and glucocorticoid-regulated kinase (SGK), and protein kinase C. The upstream kinase phosphorylating the regulatory site of Akt/PKB near the carboxy terminus has not been identified yet, but recent reports imply a role for the integrin-linked kinase (ILK-1), a serine/threonine protein kinase, or autophosphorylation.

Inhibition of Akt activation and activity can be achieved by inhibiting PI3K with inhibitors such as LY294002 and wortmannin. However, PI3K inhibition has the potential to indiscriminately affect not just all three Akt isozymes but also other PH domain-containing signaling molecules that are dependent on PdtIns(3,4,5)-P3, such as the Tec family of tyrosine kinases. Furthermore, it has been disclosed that Akt can be activated by growth signals that are independent of PI3K.

Alternatively, Akt activity can be inhibited by blocking the activity of the upstream kinase PDK1. The compound UCN-01 is a reported inhibitor of PDK1. *Biochem. J.* 375(2):255 (2003). Again, inhibition of PDK1 would result in inhibition of multiple protein kinases whose activities depend on PDK1, such as atypical PKC isoforms, SGK, and S6 kinases (Williams et al. *Curr. Biol.* 10:439-448 (2000).

Small molecule inhibitors of Akt are useful in the treatment of tumors, especially those with activated Akt (e.g. PTEN null tumors and tumors with ras mutations). PTEN is a critical negative regulator of Akt and its function is lost in many cancers, including breast and prostate carcinomas, glioblastomas, and several cancer syndromes including Bannayan-Zonana syndrome (Maehama, T. et al. *Annual Review of Biochemistry*, 70: 247 (2001)), Cowden disease (Parsons, R.; Simpson, L. *Methods in Molecular Biology* (Totowa, N.J., United States), 222 (*Tumor Suppressor Genes*, Volume 1): 147 (2003)), and Lhermitte-Duclos disease (Backman, S. et al. *Current Opinion in Neurobiology*, 12(5): 516 (2002)). Akt3 is up-regulated in estrogen receptor-deficient breast cancers and androgen-independent prostate cancer cell lines and Akt2 is over-expressed in pancreatic and ovarian carcinomas. Akt1 is amplified in gastric cancers (Staal, *Proc. Natl. Acad. Sci. USA* 84: 5034-7 (1987) and upregulated in breast cancers (Stal et al. *Breast Cancer Res.* 5: R37-R44 (2003)). Therefore a small molecule Akt inhibitor is expected to be useful for the treatment of these types of cancer as well as other types of cancer. Akt inhibitors are also useful in combination with further chemotherapeutic and anticancer agents.

It is an object of the instant invention to provide novel compounds that are inhibitors of Akt/PKB.

It is also an object of the present invention to provide pharmaceutical compositions that comprise a pharmaceutical carrier and compounds useful in the methods of the invention.

It is also an object of the present invention to provide a method for treating cancer that comprises administering such inhibitors of Akt/PKB activity.

It is also an object of the present invention to provide a method for treating arthritis that comprises administering such inhibitors of Akt/PKB activity.

SUMMARY OF THE INVENTION

This invention relates to novel compounds of Formula (I):

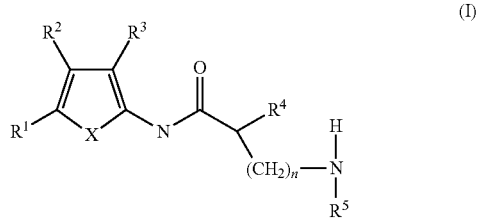

wherein:
$R^1$ and $R^2$ are independently selected from: hydrogen,

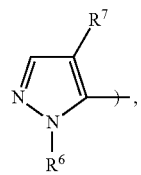

halogen and $C_{1-4}$alkyl,
where $R^6$ is $C_{1-4}$alkyl and $R^7$ is selected from hydrogen, $C_{1-4}$alkyl and halogen;
$R^3$ is selected from: hydrogen, halogen and $C_{1-4}$alkyl;
$R^4$ is selected from —$(CH_2)_m$aryl and —$(CH_2)_m$aryl wherein the aryl is substituted, where m is 0 to 2;
$R^5$ is selected from hydrogen and $C_{1-4}$alkyl;
X is selected from O and S; and
n is 0 to 2;
provided that one and only one of $R^1$ and $R^2$ is

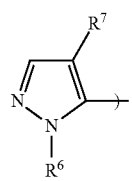

and further provided that at least one of $R^1$, $R^2$ and $R^3$ is hydrogen;
or a salt thereof.

This invention also relates to pharmaceutically acceptable salts of the compounds of Formula (I).

This invention relates to a method of treating cancer, which comprises administering to a subject in need thereof an effective amount of an Akt/PKB inhibiting compound of Formula (I).

This invention relates to a method of treating arthritis, which comprises administering to a subject in need thereof an effective amount of an Akt/PKB inhibiting compound of Formula (I).

The present invention also relates to the discovery that the compounds of Formula (I) are active as inhibitors of Akt/PKB.

In a further aspect of the invention there is provided novel processes and novel intermediates useful in preparing the presently invented Akt/PKB inhibiting compounds.

Included in the present invention are pharmaceutical compositions that comprise a pharmaceutical carrier and compounds useful in the methods of the invention.

Also included in the present invention are methods of co-administering the presently invented Akt/PKB inhibiting compounds with further active ingredients.

DETAILED DESCRIPTION OF THE INVENTION

This invention relates to compounds of Formula (I) as described above.

The presently invented compounds of Formula (I) inhibit Akt/PKB activity. In particular, the compounds disclosed herein inhibit each of the three Akt/PKB isoforms.

Included in the presently invented compounds of Formula (I) are compounds of Formula (II):

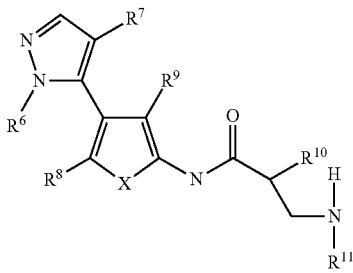

(II)

wherein:
$R^8$ and $R^9$ are independently selected from: hydrogen, halogen, and $C_{1-4}$alkyl;
$R^6$ is $C_{1-4}$alkyl;
$R^7$ is selected from hydrogen, $C_{1-4}$alkyl and halogen;
$R^{10}$ is selected from: —$(CH_2)_mC_5$-$C_{12}$aryl and —$(CH_2)_mC_5$-$C_{12}$aryl wherein the aryl is substituted, where m is 0 to 2;
$R^{11}$ is selected from hydrogen and $C_{1-4}$alkyl;
X is selected from O and S; and
provided that at least one of $R^8$ and $R^9$ is hydrogen;
or a salt thereof.

This invention also relates to pharmaceutically acceptable salts of the compounds of Formula (II).

Included in the presently invented compounds of Formula (I) are compounds of Formula (III):

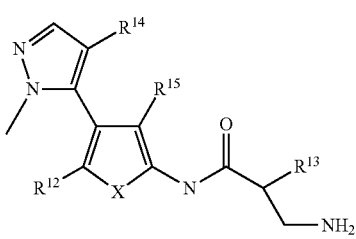

(III)

wherein:
$R^{12}$ and $R^{15}$ independently selected from: hydrogen, halogen, and $C_{1-4}$alkyl;
$R^{13}$ is selected from: —$(CH_2)_m$phenyl and —$(CH_2)_m$phenyl wherein the phenyl is substituted, where m is 0 to 2;
$R^{14}$ is selected from hydrogen, $C_{1-4}$alkyl and halogen;
provided that at least one of $R^{12}$ and $R^{15}$ is hydrogen;
X is selected from O and S; and
or a salt thereof.

This invention also relates to pharmaceutically acceptable salts of the compounds of Formula (III).

Included among the compounds useful in the present invention are:
3-amino-N-[5-chloro-4-(4-chloro-1-methyl-1H-pyrazol-5-yl)-2-thienyl]-2-phenylpropanamide;
3-amino-N-[5-chloro-4-(4-chloro-1-methyl-1H-pyrazol-5-yl)-2-thienyl]-2-(phenylmethyl)propanamide;
(2S)-3-amino-N-[5-chloro-4-(4-chloro-1-methyl-1H-pyrazol-5-yl)-2-thienyl]-2-(phenylmethyl)propanamide;
(2R)-3-amino-N-[5-chloro-4-(4-chloro-1-methyl-1H-pyrazol-5-yl)-2-thienyl]-2-(phenylmethyl)propanamide;
3-amino-N-[3,5-dichloro-4-(1-methyl-1H-pyrazol-5-yl)-2-thienyl]-2-phenylpropanamide;
3-amino-N-[3,5-dichloro-4-(1-methyl-1H-pyrazol-5-yl)-2-thienyl]-2-(phenylmethyl)propanamide;
(2S)-3-amino-N-[5-chloro-4-(4-chloro-1-methyl-1H-pyrazol-5-yl)-2-thienyl]-2-[(3,4-difluorophenyl)methyl]propanamide;
(2R)-3-amino-N-[5-chloro-4-(4-chloro-1-methyl-1H-pyrazol-5-yl)-2-thienyl]-2-[(3,4-difluorophenyl)methyl]propanamide;
(2S)-3-amino-N-[5-chloro-4-(4-chloro-1-methyl-1H-pyrazol-5-yl)-2-thienyl]-2-[(2-fluorophenyl)methyl]propanamide;
(2R)-3-amino-N-[5-chloro-4-(4-chloro-1-methyl-1H-pyrazol-5-yl)-2-thienyl]-2-[(2-fluorophenyl)methyl]propanamide;
(2S)-3-amino-N-[5-chloro-4-(4-chloro-1-methyl-1H-pyrazol-5-yl)-2-thienyl]-2-[(4-fluorophenyl)methyl]propanamide;
(2R)-3-amino-N-[5-chloro-4-(4-chloro-1-methyl-1H-pyrazol-5-yl)-2-thienyl]-2-[(4-fluorophenyl)methyl]propanamide;
(2S)-3-amino-N-[5-chloro-4-(4-chloro-1-methyl-1H-pyrazol-5-yl)-2-thienyl]-2-[(3-fluorophenyl)methyl]propanamide; and
(2R)-3-amino-N-[5-chloro-4-(4-chloro-1-methyl-1H-pyrazol-5-yl)-2-thienyl]-2-[(3-fluorophenyl)methyl]propanamide;
or a salt thereof including a pharmaceutically acceptable salt thereof.

Compounds of Formula (I) are included in the pharmaceutical compositions of the invention and used in the methods of the invention.

Certain of the compounds described herein may contain one or more chiral atoms, or may otherwise be capable of existing as two enantiomers. Accordingly, the compounds of this invention include mixtures of enantiomers as well as purified enantiomers or enantiomerically enriched mixtures. Also, it is understood that all tautomers and mixtures of tautomers are included within the scope of the compounds of Formula (I).

Certain compounds described herein may form a solvate which is understood to be a complex of variable stoichiometry formed by a solute (in this invention, a compound of Formula I a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

By the term "aryl", and derivatives thereof, used alone or as part of a larger moiety as in "—$(CH_2)_m$aryl" as used herein, unless otherwise defined, is meant monocyclic, bicyclic, and tricyclic ring systems having a total of five to fourteen ring members, wherein at least one ring system is aromatic and wherein each ring in the system contains 3 to 7 members, such as phenyl, naphthalene, tetrahydronaphthalene and biphenyl.

Suitably, by the term "aryl" is meant a monocyclic aromatic ring system having a total of five to 7 ring members.

By the term "heteroaryl", and derivatives thereof, used alone or as part of a larger moiety as in "—$(CH_2)_m$heteroaryl" as used herein, unless otherwise defined, is meant a cyclic aromatic ring containing from 3 to 7 carbon atoms and containing from one to 3 heteroatoms, provided that when the number of carbon atoms is 3 the aromatic ring contains at least two heteroatoms. Exemplary "heteroaryl" groups include pyridine and indole.

By the term "cycloalkyl", and derivatives thereof, used alone or as part of a larger moiety as in "—(CH$_2$)$_m$cycloalkyl" as used herein, unless otherwise defined, is meant a non-aromatic cyclic hydrocarbon ring having from three to seven carbon atoms. Exemplary "cycloalkyl" groups include cyclopropyl, cyclobutyl, cyclopentyl, and cyclohexyl.

By the term "heterocycloalkyl", and derivatives thereof, used alone or as part of a larger moiety as in "—(CH$_2$)$_m$heterocycloalkyl" as used herein, unless otherwise defined, is meant a non-aromatic cyclic hydrocarbon ring having from three to six carbon atoms and containing 1 or 2 heteroatoms. Exemplary "cycloalkyl" groups include piperazine and pyrrolidine.

By the term "C$_5$-C$_{12}$aryl", used alone or as part of a larger moiety as in "—(CH$_2$)$_m$C$_5$-C$_{12}$aryl", as used herein, is meant an aromatic group selected from: phenyl, naphthalene, tehrahydronaphthanlene and biphenyl.

The term "substituted" as used herein, unless otherwise defined, is meant that the subject chemical moiety has from one to five substituents, suitably from one to three substituents, selected from the group consisting of: —CO$_2$R$^{20}$, C$_1$-C$_4$alkyl, hydroxyC$_1$-C$_4$alkyl, C$_1$-C$_4$alkyloxy, amino, C$_1$-C$_4$alkylamino, aminoC$_1$-C$_4$alkyl, diC$_1$-C$_4$alkylamino, hydroxy, nitro, tetrazole, cyano, oxo, halogen and trifluoromethyl, where R$^{20}$ is selected form hydrogen, C$_1$-C$_4$alkyl, and trifluoromethyl.

Suitably, the term "substituted" as used herein is meant that the subject chemical moiety has from one to three substituents, selected from the group consisting of: C$_1$-C$_4$alkyl, hydroxyC$_1$-C$_4$alkyl, C$_1$-C$_4$alkyloxy, amino, C$_1$-C$_4$alkylamino, aminoC$_1$-C$_4$alkyl, hydroxy, tetrazole, halogen and trifluoromethyl.

Suitably, the term "substituted" as used herein is meant that the subject chemical moiety has from one to three substituents, selected from the group consisting of: halogen and trifluoromethyl.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein, including alkyl chains defined by the term "—(CH$_2$)$_n$", "—(CH$_2$)$_m$" and the like, is meant a linear or branched, saturated or unsaturated hydrocarbon chain, and unless otherwise defined, the carbon chain will contain from 1 to 12 carbon atoms. Examples of alkyl as used herein include: —CH$_3$, —CH$_2$—CH$_3$, —CH$_2$—CH$_2$—CH$_3$, —CH(CH$_3$)$_2$, —CH$_2$—CH$_2$—C(CH$_3$)$_3$, —C≡C—C(CH$_3$)$_3$, —C(CH$_3$)$_3$, —(CH$_2$)$_3$—CH$_3$, —CH$_2$—CH(CH$_3$)$_2$, —CH(CH$_3$)—CH$_2$—CH$_3$, —CH=CH$_2$, and —C≡C—CH$_3$.

By the term "treating" and derivatives thereof as used herein, is meant prophylactic and therapeutic therapy. Prophylactic therapy is appropriate, for example, when a subject is considered at high risk for developing cancer, or when a subject has been exposed to a carcinogen.

As used herein, the term "effective amount" and derivatives thereof means that amount of a drug or pharmaceutical agent that will elicit the biological or medical response of a tissue, system, animal or human that is being sought, for instance, by a researcher or clinician. Furthermore, the term "therapeutically effective amount" and derivatives thereof means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Compounds of Formula (I) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or pro-drug formulations.

The salts of the compounds of the invention are readily prepared by those of skill in the art.

The pharmaceutically acceptable salts of the compounds of the invention are readily prepared by those of skill in the art.

The novel compounds of Formula (I) are generally prepared as shown in Schemes 1 to 3 below, or by analogous methods, provided the X and 'R' substituents in Formula (I) do not include any such substituents that render inoperative the processes of any of Schemes 1 to 3. All of the starting materials are commercially available or are readily made from commercially available starting materials by those of skill in the art unless otherwise noted in the experimental section.

General Schemes

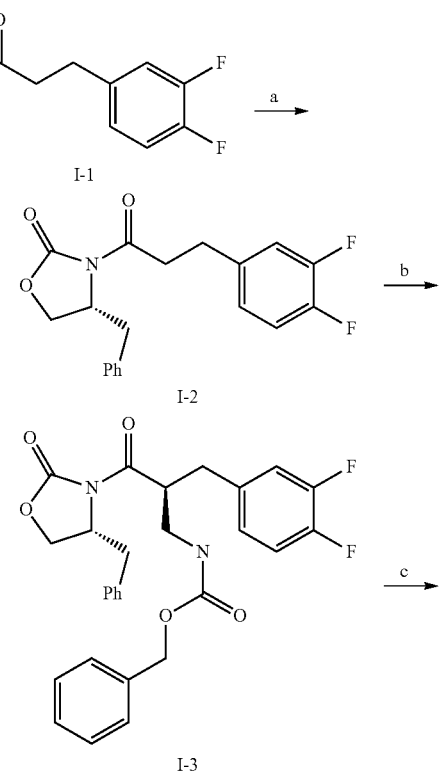

Scheme 1

-continued

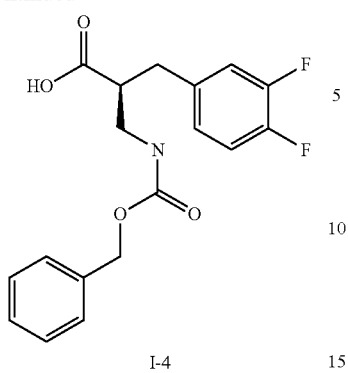

I-4

Reagents: (a) THF, Et$_3$N, -78° C., PivCl then (4R)-4-(phenylmethyl)-1, 3-oxazolidin-2-one pretreated with nBuLi, -78° C.; (b) (i) TiCl$_4$, DCM, -60° C. (ii) DIPEA, -60° C. (iii) phenylmethyl [(methyloxy)methyl]carbamate, 0° C.; (c) 30% H$_2$O$_2$, 0.8M LiOH, THF, H$_2$O, 0 to 25° C.

Acid (I-1) was converted to the mixed anhydride which was displaced with the anion of the chiral auxiliary forming the dione (I-2). The pendant amine was introduced in high diastereomeric purity according to the procedure of Evans et al [*J. Am. Chem. Soc.* 1990, 112, 8215] forming amine (I-3). The auxiliary was subsequently removed using peroxide under basic conditions generating the β-amino acid (I-4).

Scheme 2

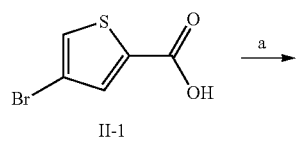

II-1

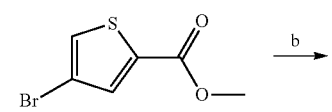

II-2

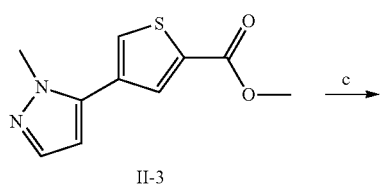

II-3

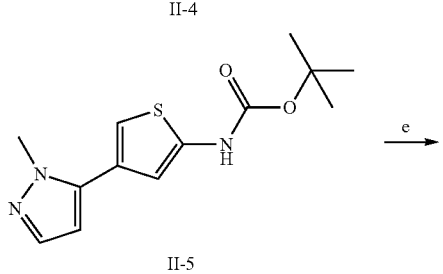

II-4

-continued

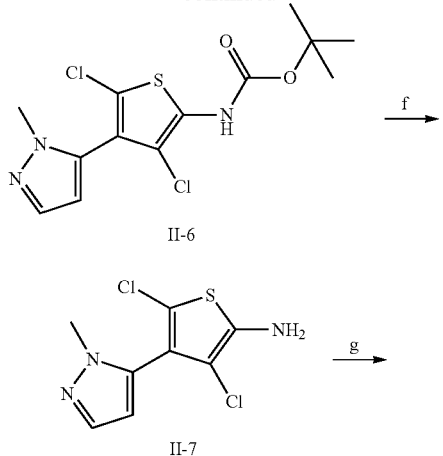

II-6

II-7

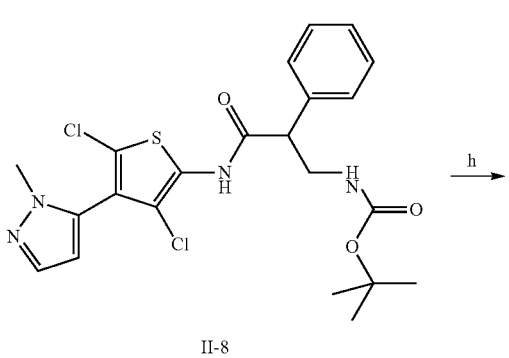

II-8

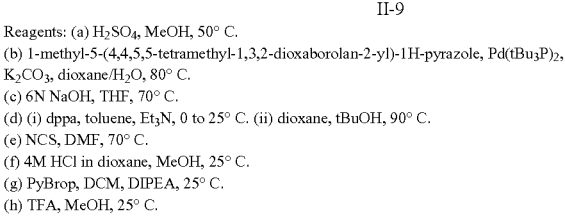

II-9

Reagents: (a) H$_2$SO$_4$, MeOH, 50° C.
(b) 1-methyl-5-(4,4,5,5-tetramethyl-1,3,2-dioxaborolan-2-yl)-1H-pyrazole, Pd(tBu$_3$P)$_2$, K$_2$CO$_3$, dioxane/H$_2$O, 80° C.
(c) 6N NaOH, THF, 70° C.
(d) (i) dppa, toluene, Et$_3$N, 0 to 25° C. (ii) dioxane, tBuOH, 90° C.
(e) NCS, DMF, 70° C.
(f) 4M HCl in dioxane, MeOH, 25° C.
(g) PyBrop, DCM, DIPEA, 25° C.
(h) TFA, MeOH, 25° C.

4-bromo-2-thiophenecarboxylic acid (II-1) underwent Fischer esterification to the ester (II-2). Suzuki coupling afforded the pyrzole thiophene ester (II-3). Next, the ester was hydrolyzed and the resulting acid (II-4) underwent a Curtius rearrangement the Boc-carbamate (II-5). Exposure to 2-fold excess NCS regioselectively afforded the dichloro thiophene (II-6). Removal of the Boc protecting group followed by coupling of the amine (II-7) with an appropriate acid provided amide (II-8). Removal of the protecting group on pendant amine yielded the reverse amide analogs (II-9).

Scheme 3

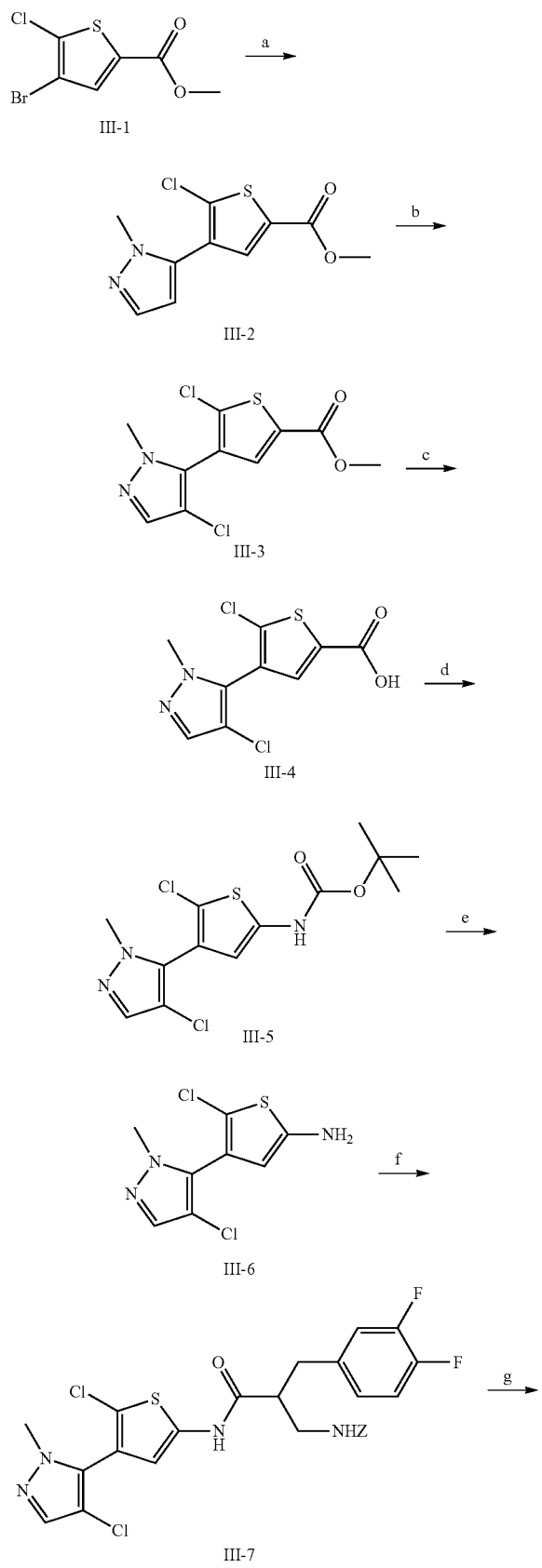

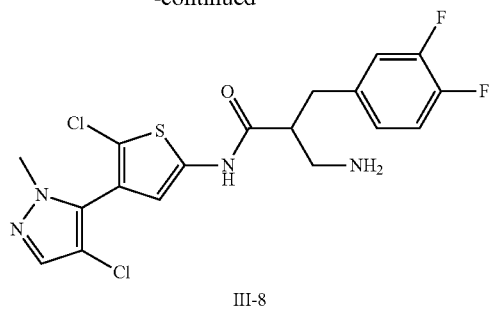

Reagents: (a) 1-methyl-5-(4,4,5,5-tetramethyl-1,3,2-dioxaborolan-2-yl)-1H-pyrazole, Pd(tBu₃P)₂, K₂CO₃, dioxane/H₂O, 80° C.
(b) NCS, THF, 70° C.
(c) 6N NaOH, THF, 70° C.
(d) (i) dppa, toluene, Et₃N, 0 to 25° C. (ii) dioxane, tBuOH, 90° C.
(e) 4M HCl in dioxane, MeOH, 25° C.
(f) PyBrop, DCM, DIPEA, 25° C.
(g) TFA, thioanisole, 25° C.

Methyl 4-bromo-5-chloro-2-thiophenecarboxylate (III-1) underwent Suzuki coupling to generate the pyrazole (III-2). Treatment with NCS provided the dichloro thiophene (III-3). Hydrolysis of the ester to the acid (III-4) and subsequent Curtius rearrangement yielded the Boc carbamate (III-5). Removal of the Boc protecting group and coupling of the amine (III-6) with an appropriate β-amino acid provided the amide (III-7). The benzyl carbamate protecting group was removed under acidic conditions affording the final reverse amide analogs (III-8).

By the term "co-administering" and derivatives thereof as used herein is meant either simultaneous administration or any manner of separate sequential administration of an AKT inhibiting compound, as described herein, and a further active ingredient or ingredients, known to be useful in the treatment of cancer, including chemotherapy and radiation treatment, or to be useful in the treatment of arthritis. The term further active ingredient or ingredients, as used herein, includes any compound or therapeutic agent known to or that demonstrates advantageous properties when administered to a patient in need of treatment for cancer or arthritis. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients (antineoplastic agent) for use in combination or co-administered with the presently invented AKT inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)-N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750, 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)-N-carboxy-3-phenylisoserine, N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R-(R*,R*)-2,3-dihydroxybutanedioate (1:2)(salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2–)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of Streptomyces verticillus, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer.

Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,1'-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I: DNA: irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

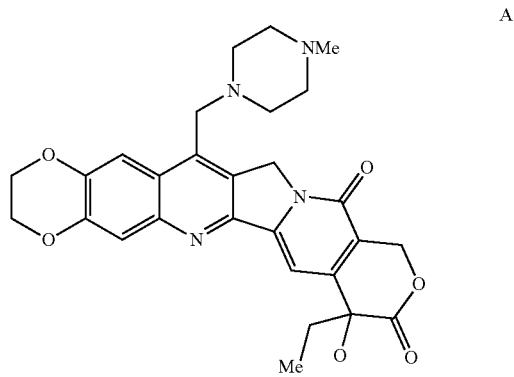 [SMILES: CCC1(O)C(=O)OCc2c1cc1n(c2=O)Cc2c-1nc1cc3c(cc1c2CN1CCN(C)CC1)OCCO3]

known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-lacaci, L., et al, Int. J. Cancer (2000), 88(1), 44-52. Additional Serine/Threonine Kinasies useful in the treatment of cancer include: Polo-like kinases (PLK), particularly PLK1; PAK1; and CENPE.

Inhibitors of Phosphotidyl inositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast Cancer Res., 2000, 2(3), 176-183); and 2CB VEGFR2 specific antibody (see Brekken, R. A. et al, Selective Inhibition of VEGFR2Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of Formula (I) and/or a pharmaceutically acceptable salt thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

Because the pharmaceutically active compounds of the present invention are active as AKT inhibitors they exhibit therapeutic utility in treating cancer and arthritis.

Suitably, the present invention relates to a method for treating or lessening the severity of a cancer selected from: brain (gliomas), glioblastomas, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Suitably, the present invention relates to a method for treating or lessening the severity of a cancer selected from: brain (gliomas), glioblastomas, Bannayan-Zonana syndrome, Cowden disease, Lhermitte-Duclos disease, breast, colon, head and neck, kidney, lung, liver, melanoma, ovarian, pancreatic, prostate, sarcoma and thyroid.

Suitably, the present invention relates to a method for treating or lessening the severity of a cancer selected from ovarian, breast, pancreatic and prostate.

Isolation and Purification of His-tagged AKT1 (aa 136-480)

Insect cells expressing His-tagged AKT1 (aa 136-480) were lysed in 25 mM HEPES, 100 mM NaCl, 20 mM imidazole; pH 7.5 using a polytron (5 mLs lysis buffer/g cells). Cell debris was removed by centrifuging at 28,000×g for 30 minutes. The supernatant was filtered through a 4.5-micron filter then loaded onto a nickel-chelating column pre-equilibrated with lysis buffer. The column was washed with 5 column volumes (CV) of lysis buffer then with 5 CV of 20% buffer B, where buffer B is 25 mM HEPES, 100 mM NaCl, 300 mM imidazole; pH 7.5. His-tagged AKT1 (aa 136-480) was eluted with a 20-100% linear gradient of buffer B over 10 CV. His-tagged AKT1 (136-480) eluting fractions were pooled and diluted 3-fold with buffer C, where buffer C is 25 mM HEPES, pH 7.5. The sample was then chromatographed over a Q-Sepharose HP column pre-equilibrated with buffer C. The column was washed with 5 CV of buffer C then step eluted with 5 CV 10% D, 5 CV 20% D, 5 CV 30% D, 5 CV 50% D and 5 CV of 100% D; where buffer D is 25 mM HEPES, 1000 mM NaCl; pH 7.5. His-tagged AKT1 (aa 136-480) containing fractions were pooled and concentrated in a 10-kDa molecular weight cutoff concentrator. His-tagged AKT1 (aa 136-480) was chromatographed over a Superdex 75 gel filtration column pre-equilibrated with 25 mM HEPES, 200 mM NaCl, 1 mM DTT; pH 7.5. His-tagged AKT1 (aa 136-480) fractions were examined using SDS-PAGE and mass spec. The protein was pooled, concentrated and frozen at −80 C.

His-tagged AKT2 (aa 138-481) and His-tagged AKT3 (aa 135-479) were isolated and purified in a similar fashion.

His-tagged AKT Enzyme Assay

Compounds of the present invention were tested for AKT 1, 2, and 3 protein serine kinase inhibitory activity in substrate phosphorylation assays. This assay examines the ability of small molecule organic compounds to inhibit the serine phosphorylation of a peptide substrate. The substrate phosphorylation assays use the catalytic domains of AKT 1, 2, or 3. AKT 1, 2 and 3 are also commercially available from Upstate USA, Inc. The method measures the ability of the isolated enzyme to catalyze the transfer of the gamma-phosphate from ATP onto the serine residue of a biotinylated synthetic peptide SEQ.ID NO: 1 (Biotin-ahx-ARKRERAYSFGHHA-amide). Substrate phosphorylation was detected by the following procedure:

Assays were performed in 384 well U-bottom white plates. 10 nM activated AKT enzyme was incubated for 40 minutes at room temperature in an assay volume of 20 ul containing 50 mM MOPS, pH 7.5, 20 mM $MgCl_2$, 4 uM ATP, 8 uM peptide, 0.04 uCi [g-$^{33}$P] ATP/well, 1 mM CHAPS, 2 mM DTT, and 1 ul of test compound in 100% DMSO. The reaction was stopped by the addition of 50 ul SPA bead mix (Dulbecco's PBS without $Mg^{2+}$ and $Ca^{2+}$, 0.1% Triton X-100, 5 mM EDTA, 50 uM ATP, 2.5 mg/ml Streptavidin-coated SPA beads.) The plate was sealed, the beads were allowed to settle overnight, and then the plate was counted in a Packard Topcount Microplate Scintillation Counter (Packard Instrument Co., Meriden, Conn.).

The data for dose responses were plotted as % Control calculated with the data reduction formula $100*(U1-C2)/(C1-C2)$ versus concentration of compound where U is the unknown value, C1 is the average control value obtained for DMSO, and C2 is the average control value obtained for 0.1M EDTA. Data are fitted to the curve described by: $y=((Vmax*x)/(K+x))$ where Vmax is the upper asymptote and K is the IC50.

Cloning of Full-length Human (FL) AKT1:

Full-length human AKT1 gene was amplified by PCR from a plasmid containing myristylated-AKT1-ER (gift from Robert T. Abraham, Duke University under MTA, described in Klippel et al. in Molecular and Cellular Biology 1998 Volume 18 p. 5699) using the 5' primer: SEQ.ID NO: 2, 5' TATATAGGATCCATGAGCGACGTGGC 3' and the 3' primer: SEQ.ID NO: 3, AAATTTCTCGAGTCAGGCCGTGCTGCTGG 3'. The 5' primer included a BamHI site and the 3' primer included an XhoI site for cloning purposes. The resultant PCR product was subcloned in pcDNA3 as a BamHI/XhoI fragment. A mutation in the sequence (TGC) coding for a Cysteine[25] was converted to the wild-type AKT1 sequence (CGC) coding for an Arginine[25] by site-directed mutagenesis using the QuikChange® Site Directed Mutagenesis Kit (Stratagene). The AKT1 mutagenic primer: SEQ.ID NO: 4, 5' ACCTGGCGGCCACGCTACTTCCTCC and selection primer: SEQ.ID NO: 5, 5' CTCGAGCATGCAACTAGAGGGCC (designed to destroy an XbaI site in the multiple cloning site of pcDNA3) were used according to manufacturer's suggestions. For expression/purification purposes, AKT1 was isolated as a BamHI/XhoI fragment and cloned into the BamHI/XhoI sites of pFastbacHTb (Invitrogen).

Expression of FL Human AKT1:

Expression was done using the BAC-to-BAC Baculovirus Expression System from Invitrogen (catalog #10359-016). Briefly 1) the cDNA was transferred from the FastBac vector into bacmid DNA, 2) the bacmid DNA was isolated and used to transfect Sf9 insect cells, 3) the virus was produced in Sf9 cells, 4) T. ni cells were infected with this virus and sent for purification.

Purification of FL Human AKT1:

For the purification of full-length AKT1, 130 g sf9 cells (batch #41646WO2) were resuspended in lysis buffer (buffer A, 1 L, pH 7.5) containing 25 mM HEPES, 100 mM NaCl, and 20 mM imidazole. The cell lysis was carried out by Avestin (2 passes at 15K-20K psi). Cell debris was removed by centrifuging at 16K rpm for 1 hour and the supernatant was batch bound to 10 ml Nickel Sepharose HP beads at 4 C for over night. The beads were then transferred to column and the bound material was eluted with buffer B (25 mM HEPES, 100 mM NaCl, 300 mM imidazole, pH 7.5). AKT eluting fractions were pooled and diluted 3 fold using buffer C (25 mM HEPES, 5 mM DTT; pH 7.5). The sample was filtered and chromatographed over a 10 mL Q-HP column pre-equilibrated with buffer C at 2 mL/min.

The Q-HP column was washed with 3 column volume (CV) of buffer C, then step eluted with 5 CV 10% D, 5 CV 20% D, 5 CV 30% D, 5 CV 50% D and 5 CV of 100% D; where buffer D is 25 mM HEPES, 1000 mM NaCl, 5 mM DTT; pH 7.5. 5 mL fractions collected. AKT containing fractions were pooled and concentrated to 5 ml. The protein was next loaded to a 120 ml Superdex 75 sizing column that was pre-equilibrated with 25 mM HEPES, 200 mM NaCl, 5 mM DTT; pH 7.5. 2.5 mL fractions were collected.

AKT 1 eluting fractions were pooled, aliquoted (1 ml) and stored at −80 C. Mass spec and SDS-PAGE analysis were used to confirm purity and identity of the purified full-length AKT1.

Full length AKT2 and full length AKT3 were cloned, expressed and purified in a similar fashion.

AKT Enzyme Assay

Compounds of the present invention are tested for AKT 1, 2, and 3 protein serine kinase inhibitory activity in substrate phosphorylation assays. This assay examines the ability of small molecule organic compounds to inhibit the serine phosphorylation of a peptide substrate. The substrate phosphorylation assays use the catalytic domains of AKT 1, 2, or 3. AKT 1, 2 and 3 are also commercially available from Upstate USA, Inc. The method measures the ability of the isolated enzyme to catalyze the transfer of the gamma-phosphate from ATP onto the serine residue of a biotinylated synthetic peptide SEQ. ID NO: 5 (Biotin-ahx-ARKRERAYSFGHHA-amide). Substrate phosphorylation is detected by the following procedure:

Assays are performed in 384 well U-bottom white plates. 10 nM activated AKT enzyme is incubated for 40 minutes at room temperature in an assay volume of 20 ul containing 50 mM MOPS, pH 7.5, 20 mM $MgCl_2$, 4 uM ATP, 8 uM peptide, 0.04 uCi [g-$^{33}$P] ATP/well, 1 mM CHAPS, 2 mM DTT, and 1 ul of test compound in 100% DMSO. The reaction is stopped by the addition of 50 ul SPA bead mix (Dulbecco's PBS without $Mg^{2+}$ and $Ca^{2+}$, 0.1% Triton X-100, 5 mM EDTA, 50 uM ATP, 2.5 mg/ml Streptavidin-coated SPA beads.) The plate is sealed, the beads are allowed to settle overnight, and then the plate is counted in a Packard Topcount Microplate Scintillation Counter (Packard Instrument Co., Meriden, Conn.).

The data for dose responses are plotted as % Control calculated with the data reduction formula $100*(U1-C2)/(C1-C2)$ versus concentration of compound where U is the unknown value, C1 is the average control value obtained for DMSO, and C2 is the average control value obtained for 0.1M EDTA. Data are fitted to the curve described by: y=((Vmax*x)/(K+x)) where Vmax is the upper asymptote and K is the IC50.

Compounds of the invention are tested for activity against AKT1, AKT2, and AKT3 in one or more of the above assays.

The compounds of the Examples were tested generally according to the above AKT enzyme assays and in at least one experimental run exhibited a pIC50 value: ≥6.4 against full length AKT1.

The compound of Example 1 was tested generally according to the above AKT enzyme assays and in at least one experimental run exhibited a pIC50 value: equal to 6.8 against full length AKT1.

The compound of Example 5 was tested generally according to the above AKT enzyme assays and in at least one experimental run exhibited a pIC50 value: equal to 8.0 against full length AKT1.

The compound of Example 7 was tested generally according to the above AKT enzyme assays and in at least one experimental run exhibited a pIC50 value: equal to 8.8 against full length AKT1.

The compound of Example 10 was tested generally according to the above AKT enzyme assays and in at least one experimental run exhibited a pIC50 value: equal to 8.3 against full length AKT1.

The compound of Example 13 was tested generally according to the above AKT enzyme assays and in at least one experimental run exhibited a pIC50 value: equal to 8.6 against full length AKT1.

In the above data, pIC50 is defined as −log(IC50) where the IC50 value is expressed in molar units.

The pharmaceutically active compounds within the scope of this invention are useful as AKT inhibitors in mammals, particularly humans, in need thereof.

The present invention therefore provides a method of treating cancer, arthritis and other conditions requiring AKT inhibition, which comprises administering an effective compound of Formula (I) and/or a pharmaceutically acceptable salt, hydrate, solvate or pro-drug thereof. The compounds of Formula (I) also provide for a method of treating the above indicated disease states because of their demonstrated ability to act as Akt inhibitors. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of an Akt inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages, is preferred. Parenteral administration, at high dosages, however, also can be used when safe and convenient for the patient.

Optimal dosages to be administered may be readily determined by those skilled in the art, and will vary with the particular Akt inhibitor in use, the strength of the preparation, the mode of administration, and the advancement of the disease condition. Additional factors depending on the particular patient being treated will result in a need to adjust dosages, including patient age, weight, diet, and time of administration.

The method of this invention of inducing Akt inhibitory activity in mammals, including humans, comprises administering to a subject in need of such activity an effective Akt inhibiting amount of a pharmaceutically active compound of the present invention.

The invention also provides for the use of a compound of Formula (I) in the manufacture of a medicament for use as an Akt inhibitor.

The invention also provides for the use of a compound of Formula (I) in the manufacture of a medicament for use in therapy.

The invention also provides for the use of a compound of Formula (I) in the manufacture of a medicament for use in treating cancer.

The invention also provides for the use of a compound of Formula (I) in the manufacture of a medicament for use in treating arthritis.

The invention also provides for a pharmaceutical composition for use as an Akt inhibitor which comprises a compound of Formula (I) and a pharmaceutically acceptable carrier.

The invention also provides for a pharmaceutical composition for use in the treatment of cancer which comprises a compound of Formula (I) and a pharmaceutically acceptable carrier.

The invention also provides for a pharmaceutical composition for use in treating arthritis which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat cancer or arthritis, or compounds known to have utility when used in combination with an Akt inhibitor.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

The compounds of Examples 1 to 14 are readily made according to Schemes 1 to 3 or by analogous methods.

Preparation 1

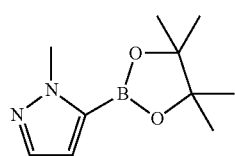

Preparation of 5-(5,5-dimethyl-1,3,2-dioxaborinan-2-yl)-1-methyl-1H-pyrazole

To a solution of 1-methylpyrazole (4.1 g, 50 mmole) in THF (100 mL) at 0° C. was added n-BuLi (2.2M in THF, 55 mmole). The reaction solution was stirred for 1 hour at RT and then cooled to −78° C. [*J. Heterocyclic Chem.* 41, 931 (2004)]. To the reaction solution was added 2-isopropoxy-4,4,5,5-tetramethyl-1,3,2-dioxaborolane (12.3 mL, 60 mmole). After 15 min at −78° C., the reaction was allowed to warm to 0° C. over 1 hour. The reaction was diluted with saturated NH$_4$Cl solution and extracted with DCM. The organic fractions were washed with H$_2$O (2×100 mL), dried over Na$_2$SO$_4$ and concentrated under vacuum to afford a tan solid (8.0 g, 77%) which was used without further purification.

LCMS (ES) m/z 127 (M+H)$^+$ for [RB(OH)$_2$]; $^1$H NMR (CDCl$_3$, 400 MHz) δ 7.57 (s, 1H), 6.75 (s, 1H), 4.16 (s, 3H), and 1.41 (s, 12H).

Preparation 2

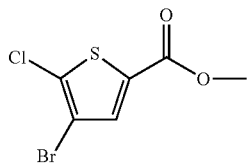

Preparation of methyl 4-bromo-5-chloro-2-thiophenecarboxylate a) methyl 5-chloro-2-thiophenecarboxylate

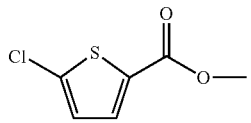

To a solution of 5-chloro-2-thiophenecarboxylic acid (10 g, 61.5 mmol) in methanol (200 ml) was added sulfuric acid (0.983 ml, 18.45 mmol). The resulting solution stirred at 50° C. overnight. H$_2$O (50 mL) was added and the reaction was cooled to 0° C. in an ice-bath. The pH was adjusted to ~12 and the aqueous phase was washed several times with DCM. The combined organic fractions were dried over Na$_2$SO$_4$, concentrated and used directly without further purification providing methyl 5-chloro-2-thiophenecarboxylate (7.2 g, 40.8 mmol, 66.3% yield): LCMS (ES) m/z 178 (M+H)$^+$.

b) methyl 4-bromo-5-chloro-2-thiophenecarboxylate

To a solution of methyl 5-chloro-2-thiophenecarboxylate (7 g, 39.6 mmol) and aluminum trichloride (7.93 g, 59.4 mmol) in chloroform (79 ml) at 25° C. was added bromine (2.86 ml, 55.5 mmol). The resulting solution stirred at 25° C. for 2 h. Ice chips were added to quench and the solution was partitioned between H$_2$O-DCM. The aqueous phase was washed several times with DCM and the combined organic fractions were dried over Na$_2$SO$_4$, concentrated and purified via column chromatography (silica, 5% EtOAc in hexanes) affording methyl 4-bromo-5-chloro-2-thiophenecarboxylate (7.2 g, 28.2 mmol, 71.1% yield) as a white solid; LCMS (ES) m/z=255, 257 (M, M+2)$^+$.

Preparation 3

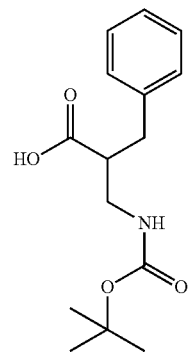 [SMILES: CC(C)(C)OC(=O)NCC(Cc1ccccc1)C(=O)O]

Preparation of 3-({[(1,1-dimethylethyl)oxy]carbonyl}amino)-2-(phenylmethyl)propanoic acid a) diethyl 2-[(1,3-dioxo-1,3-dihydro-2H-isoindol-2-yl)methyl]-2-(phenylmethyl)butanedioate

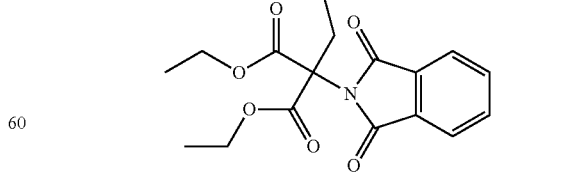

To a suspension of NaH (2.2 g, 54 mmole) in THF (200 mL) was added diethyl 2-(phenylmethyl)butanedioate (12.5 g, 49.9 mmole). After 30 min at RT, bromomethyl phthalimide was added to the reaction mixture and the contents were stirred for 14 h at RT. The reaction was quenched with H₂O (15 mL), diluted with Et₂O (300 mL) and layers separated. The organic layer was concentrated under vacuum and the resulting residue recrystallized from EtOH (0°) to give the title compound (13 g, 64%) as a white solid:

LCMS (ES) m/z 410 (M+H)⁺.

b) 3-amino-2-(phenylmethyl)propanoic acid

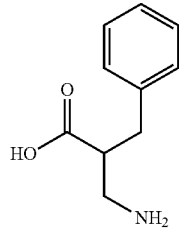 [SMILES: NCC(Cc1ccccc1)C(=O)O]

A solution of diethyl 2-[(1,3-dioxo-1,3-dihydro-2H-isoindol-2-yl)methyl]-2-(phenylmethyl)butanedioate (13 g, 31.8 mmole) in conc. HCl (125 mL) and HOAc (30 mL) was sealed in a 1 L screwcap reaction vessel and the contents heated to 120° C. for 48 h. The reaction solution was concentrated under vacuum and the resulting solids washed with Et₂O affording the title compound (quant.) as a white solid: LCMS (ES) m/z 181(M+H)⁺.

c) 3-({[(1,1-dimethylethyl)oxy]carbonyl}amino)-2-(phenylmethyl)propanoic acid

To a solution of 3-amino-2-(phenylmethyl)propanoic acid (from previous reaction) in dioxane (100 mL) and H₂O (20 mL) was added Boc anhydride (10.1 g, 46.5 mmole) and 6M NaOH solution (26 mL). After stirring at RT for 12 h, the reaction solution was concentrated under vacuum, neutralized with 3M HCl and extracted with DCM. The organic layer was dried over Na₂SO₄ and concentrated to a viscous oil. The oil was washed with pentane and dried under high vacuum to give the title compound (5.0 g, 17.9 mmole, 58% for 2 steps) as a white solid: LCMS (ES) m/z 280 (M+H)⁺.

Preparation 4

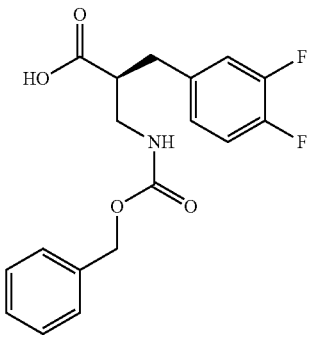 [SMILES: O=C(NC[C@H](Cc1ccc(F)c(F)c1)C(=O)O)OCc1ccccc1]

Preparation of (2S)-3-(3,4-difluorophenyl)-2-[({[(phenylmethyl)oxy]carbonyl}amino) methyl] propanoic acid a) (4R)-3-[3-(3,4-difluorophenyl)propanoyl]-4-(phenylmethyl)-1,3-oxazolidin-2-one

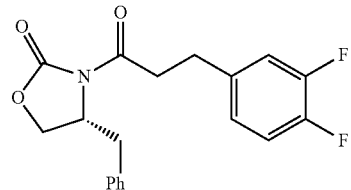 [SMILES: O=C(CCc1ccc(F)c(F)c1)N1C(=O)OC[C@H]1Cc1ccccc1]

To a solution of 3-(3,4-difluorophenyl)propanoic acid (5.25 g, 28.2 mmol) in tetrahydrofuran (157 ml) was added triethylamine (5.11 ml, 36.7 mmol). The reaction mixture was cooled to −78° C. and pivaloyl chloride (3.99 ml, 32.4 mmol) was added dropwise. The solution stirred in an ice water bath for 1 h and was cooled back down to −78° C.

In a separate flask, nbuli (12.30 ml, 30.8 mmol) was added dropwise to a −78° C. solution of (4R)-4-(phenylmethyl)-1,3-oxazolidin-2-one (5 g, 28.2 mmol) in tetrahydrofuran (78 ml). After 30 min, this solution was added via cannula to the former. Upon addition, the reaction mixture stirred at 0° C. for 30 min. and was quenched with H₂O. The aqueous phase was washed several times with DCM and the combined organic fractions were dried over Na₂SO₄, dry loaded onto silica and purified by chromatography (0-50% EtOAc in hexanes) affording (4R)-3-[3-(3,4-difluorophenyl)propanoyl]-4-(phenylmethyl)-1,3-oxazolidin-2-one (5 g, 14.48 mmol, 51.3% yield) as a white solid: LCMS (ES) m/e 310 (M+H)⁺.

b) phenylmethyl {(2S)-2-[(3,4-difluorophenyl)methyl]-3-oxo-3-[(4R)-2-oxo-4-(phenylmethyl)-1,3-oxazolidin-3-yl]propyl}carbamate

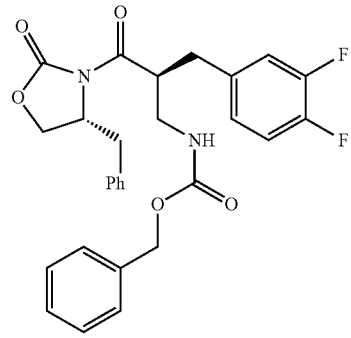 [SMILES: O=C(NC[C@H](Cc1ccc(F)c(F)c1)C(=O)N1C(=O)OC[C@H]1Cc1ccccc1)OCc1ccccc1]

To a solution of (4R)-3-[3-(3,4-difluorophenyl)propanoyl]-4-(phenylmethyl)-1,3-oxazolidin-2-one (1 g, 2.90 mmol) in dichloromethane (29.0 ml) at −60° C. was added TiCl₄ (0.335 ml, 3.04 mmol) dropwise. After 30 min, DIPEA (0.556 ml, 3.19 mmol) was added and the solution stirred at 1 h at 0° C. phenylmethyl [(methyloxy)methyl]carbamate (1.131 g, 5.79 mmol)[prepared according to Barnett, C. J. et al, *Tetrahedron Lett.* 1997, 38, 5, 735.] was added and the reaction mixture stirred at 0° C. for 4 h. The solution was quenched with aqueous saturated ammonium chloride solution and extracted several times with DCM. The combined organic fractions were dried over Na₂SO₄, concentrated and purified by column chromatography (0-50% EtOAc in hexanes) affording phenylmethyl {(2S)-2-[(3,4-difluorophenyl)methyl]-3-oxo-3-[(4R)-2-oxo-4-(phenylmethyl)-1,3-oxazolidin-3-yl]propyl}carbamate (548 mg, 0.506 mmol, 17.49% yield) as a clear oil:
LCMS (ES) m/e 430 (M+H)⁺.

c) (2S)-3-(3,4-difluorophenyl)-2-[({[(phenylmethyl)oxy]carbonyl}amino)methyl]propanoic acid To a solution of phenylmethyl {(2S)-2-[(3,4-difluorophenyl)methyl]-3-oxo-3-[(4R)-2-oxo-4-(phenylmethyl)-1,3-oxazolidin-3-yl]propyl}carbamate (548 mg, 1.078 mmol) in tetrahydrofuran (16.200 ml) and Water (5.40 ml) at 0° C. was added H₂O₂ (0.198 ml, 1.940 mmol)[30 wt %] followed by LiOH (2.69 ml, 2.155 mmol)[0.8M solution]. After 1 h, the solution warmed to 25° C. and stirred 2 h. The reaction mixture was quenched with Na₂SO₃ solution and the pH was carefully adjusted to ~3 with 2N HCl solution. The aqueous phase was washed several times with DCM and the combined organic fractions were dried over Na₂SO₄, concentrated and purified by column chromatography (10-60% EtOAc in hexanes) affording (2S)-3-(3,4-difluorophenyl)-2-[({[(phenylmethyl)oxy]carbonyl}amino)methyl]propanoic acid (260 mg, 0.700 mmol, 64.9% yield) as a clear oil: LCMS (ES) m/e 350 (M+H)⁺, ¹H NMR (400 MHz, DMSO-d6) δ ppm 12.36 (br. s., 1 H) 7.20-7.40 (m, 8 H) 7.03 (br. s., 1 H) 5.02 (s, 2 H) 4.52-4.75 (m, 1 H) 3.01-3.26 (m, 2 H) 2.77 (s, 2 H).

Example 1

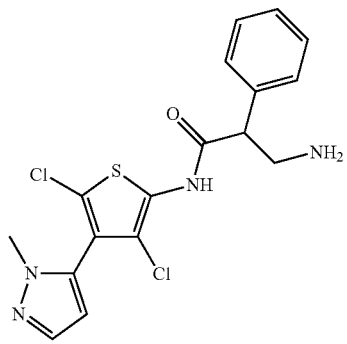 [SMILES: Cn1nccc1-c1c(Cl)sc(NC(=O)C(CN)c2ccccc2)c1Cl]

Preparation of 3-amino-N-[3,5-dichloro-4-(1-methyl-1H-pyrazol-5-yl)-2-thienyl]-2-phenylpropanamide a) methyl 4-bromo-2-thiophenecarboxylate

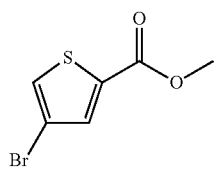

To a solution of 4-bromo-2-thiophenecarboxylic acid (25 g, 121 mmol) in methanol (241 ml) was added sulfuric acid (32.2 ml, 604 mmol). The resulting solution stirred at 50° C. over 12 h. The solution was partitioned between H₂O-DCM and the aqueous phase was washed several times with DCM. The combined organic fractions were dried over Na₂SO₄, concentrated and used directly without further purification providing methyl 4-bromo-2-thiophenecarboxylate (26 g, 118 mmol, 97% yield), LCMS (ES) m/e 222 (M+H)⁺.

b) methyl 4-(1-methyl-1H-pyrazol-5-yl)-2-thiophenecarboxylate

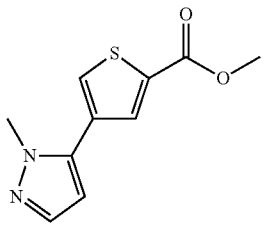

A solution of methyl 4-bromo-2-thiophenecarboxylate (2.5 g, 11.31 mmol), potassium carbonate (7.81 g, 56.5 mmol), 1-methyl-5-(4,4,5,5-tetramethyl-1,3,2-dioxaborolan-2-yl)-1H-pyrazole (2.59 g, 12.44 mmol) and bis(tri-t-butylphosphine)palladium(0) (0.289 g, 0.565 mmol) in 1,4-dioxane (47.1 ml) and water (9.42 ml) was stirred at 80° C. in a sealed tube for 1 h. The mixture was partitioned between H₂O-DCM. The aqueous phase was washed several times with DCM and the combined organic fractions were dried over Na₂SO₄, concentrated and purified via column chromatography (10-40% EtOAc in hexanes) affording methyl 4-(1-methyl-1H-pyrazol-5-yl)-2-thiophenecarboxylate (2.5 g, 11.25 mmol, 99% yield) as a yellow solid:
LCMS (ES) m/e 223 (M+H)⁺.

c) 4-(1-methyl-1H-pyrazol-5-yl)-2-thiophenecarboxylic acid

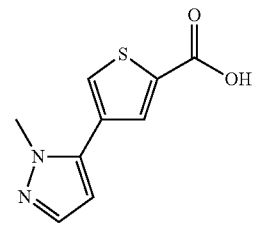

A solution of methyl 4-(1-methyl-1H-pyrazol-5-yl)-2-thiophenecarboxylate (3 g, 13.50 mmol) in 6N sodium hydroxide (22.50 ml, 135 mmol) and tetrahydrofuran (27.0 ml) was stirred in a sealed tube at 70° C. After 1 h, the solution was partitioned between H₂O-DCM and the pH of the aqueous layer was adjusted to ~3. The aqueous layer was washed several times with DCM and the combined organic fractions were dried over Na₂SO₄, concentrated affording 4-(1-methyl-1H-pyrazol-5-yl)-2-thiophenecarboxylic acid (2.8 g, 13.45 mmol, 100% yield) as a yellow solid which was used directly without further purification: LCMS (ES) m/e 209 (M+H)⁺.

d) 1,1-dimethylethyl[4-(1-methyl-1H-pyrazol-5-yl)-2-thienyl]carbamate

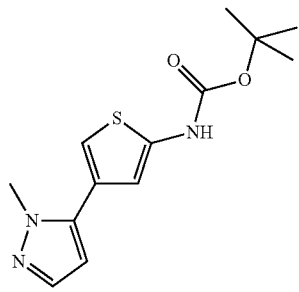 [SMILES: Cn1nccc1-c1csc(NC(=O)OC(C)(C)C)c1]

To a solution of 4-(1-methyl-1H-pyrazol-5-yl)-2-thiophenecarboxylic acid (2 g, 9.60 mmol) in acetone (80 ml) at 0° C. was added triethylamine (1.473 ml, 10.56 mmol) followed by methyl chloroformate (0.818 ml, 10.56 mmol). After 30 min, sodium azide (0.624 g, 9.60 mmol) was added in one portion and the reaction mixture warmed to 25° C. and stirred 2 h. The sodium chloride precipitate was filtered off and the filtrate was diluted with H₂O and washed several times with DCM. The combined organic fractions were dried over Na₂SO₄ and concentrated affording the acyl azide intermediate which dissolved in 1,4-Dioxane (80 ml) and tBuOH (9.19 ml, 96 mmol) and heated to 100° C. for 12 h. The solution was cooled and partitioned between H₂O-DCM and the aqueous phase was washed several times with DCM. The combined organic fractions were dried over Na₂SO₄, dry loaded onto silica and purified via chromatography (0-75% EtOAc in hexanes) affording 1,1-dimethylethyl[4-(1-methyl-1H-pyrazol-5-yl)-2-thienyl]carbamate (790 mg, 2.83 mmol, 29.4% yield) as a clear oil: LCMS (ES) m/e 280 (M+H)⁺.

e) 1,1-dimethylethyl[3,5-dichloro-4-(1-methyl-1H-pyrazol-5-yl)-2-thienyl]carbamate

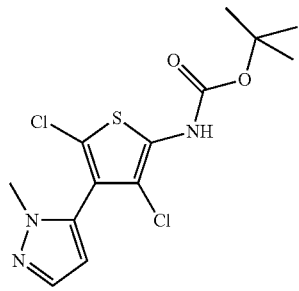 [SMILES: Cn1nccc1-c1c(Cl)sc(NC(=O)OC(C)(C)C)c1Cl]

A solution of 1,1-dimethylethyl[4-(1-methyl-1H-pyrazol-5-yl)-2-thienyl]carbamate (700 mg, 2.506 mmol) and NCS (335 mg, 2.506 mmol) in N,N-dimethylformamide (12.500 ml) was stirred in a sealed tube at 70° C. After 1 h, additional NCS (335 mg, 2.506 mmol) was added and the reaction mixture stirred 1 h. LCMS showed complete conversion to the di-chloro product. The solution was concentrated and then dry loaded onto silica and purified by chromatography (0-40% EtOAc in hexanes) affording 1,1-dimethylethyl[4-(1-methyl-1H-pyrazol-5-yl)-2-thienyl]carbamate (700 mg, 2.506 mmol) as a yellow oil: LCMS (ES) m/e 348, 350 (M, M+2)⁺, 1H NMR (400 MHz, DMSO-d₆) δ ppm 7.55 (d, J=1.77 Hz, 1 H) 6.37 (d, J=2.02 Hz, 1 H) 3.66 (s, 3 H) 1.50 (s, 9 H).

f) 3,5-dichloro-4-(1-methyl-1H-pyrazol-5-yl)-2-thiophenamine

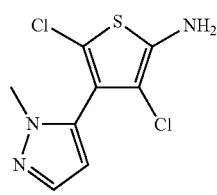

To a solution of 1,1-dimethylethyl[3,5-dichloro-4-(1-methyl-1H-pyrazol-5-yl)-2-thienyl]carbamate (700 mg, 2.010 mmol) in methanol (10.05 ml) at 25° C. was added HCl (10.100 ml, 40.4 mmol)[4M in dioxane]. After 12 h, the reaction mixture was concentrated affording the HCl salt of [3,5-dichloro-4-(1-methyl-1H-pyrazol-5-yl)-2-thienyl]amine (640 mg, 1.909 mmol, 95% yield) as a purple foam: LCMS (ES) m/e 284, 286 (M, M+2)⁺.

g) 1,1-dimethylethyl (3-{[3,5-dichloro-4-(1-methyl-1H-pyrazol-5-yl)-2-thienyl]amino}-3-oxo-2-phenylpropyl)carbamate

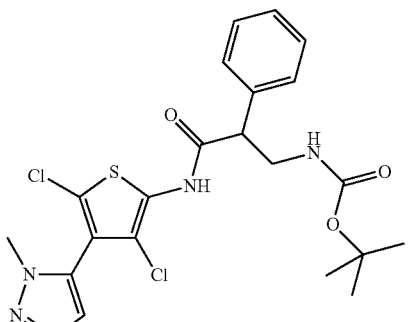

To a solution of 3-({[(1,1-dimethylethyl)oxy]carbonyl}amino)-2-phenylpropanoic acid (342 mg, 1.290 mmol), [3,5-dichloro-4-(1-methyl-1H-pyrazol-5-yl)-2-thienyl]amine (320 mg, 1.290 mmol) and DIPEA (1.126 ml, 6.45 mmol) in dichloromethane (12.100 ml) at 25° C. was added bromo-tris-pyrrolidino-phosphonium hexafluorophosphate (723 mg, 1.548 mmol) in one portion. After 12 h, additional DIPEA (1.126 ml, 6.45 mmol), 3-({[(1,1-dimethylethyl)oxy]

carbonyl}amino)-2-phenylpropanoic acid (342 mg, 1.290 mmol) and Bromo-tris-pyrrolidino-phosphonium hexafluorophosphate (723 mg, 1.548 mmol) were added and the solution stirred 24 h. The reaction mixture was then dry loaded onto silica and purified by chromatography (0-70% EtOAc in hexanes) affording 1,1-dimethylethyl (3-{[3,5-dichloro-4-(1-methyl-1H-pyrazol-5-yl)-2-thienyl]amino}-3-oxo-2-phenylpropyl)carbamate (320 mg, 0.491 mmol, 38.1% yield) as an yellow oil: LCMS (ES) m/e 495, 497 (M, M+2)+.

h) 3-amino-N-[3,5-dichloro-4-(1-methyl-1H-pyrazol-5-yl)-2-thienyl]-2-phenylpropanamide To a solution of 1,1-dimethylethyl (3-{[3,5-dichloro-4-(1-methyl-1H-pyrazol-5-yl)-2-thienyl]amino}-3-oxo-2-phenylpropyl)carbamate (320 mg, 0.646 mmol) in dichloromethane (6.459 ml) at 25° C. was added TFA (0.498 ml, 6.46 mmol). After 30 min, the solution was dry loaded onto silica and neutralized through silica (0-20% MeOH in DCM (1% NH$_4$OH) affording the free base of the title compound. The free base was then dissolved in MeOH (10 mL) and treated with excess 4M HCl in dioxane (2 mL) providing the HCl salt of 3-amino-N-[3,5-dichloro-4-(1-methyl-1H-pyrazol-5-yl)-2-thienyl]-2-phenylpropanamide (188 mg, 0.414 mmol, 64.0% yield) as an orange solid: LCMS (ES) m/e 395, 397 (M, M+2)+; $^1$H NMR (400 MHz, DMSO-d$_6$) δ ppm 11.65 (s, 1 H) 8.18 (br. s., 3 H) 7.55 (d, J=1.77 Hz, 1 H) 7.28-7.51 (m, 1 H) 7.41 (d, J=5.05 Hz, 4 H) 6.36 (d, J=6.06 Hz, 1 H) 4.53 (dd, J=9.09, 5.31 Hz, 1 H) 3.81 (br. s., 3 H) 3.48-3.59 (m, 1 H) 3.01-3.17 (m, 1 H).

Example 2

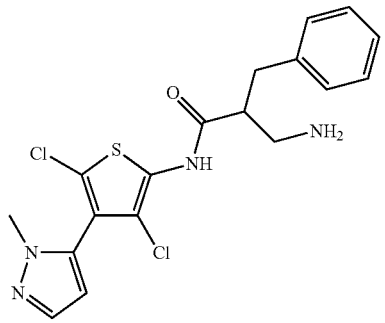 [SMILES: Cn1nccc1-c1c(Cl)sc(NC(=O)C(CN)Cc2ccccc2)c1Cl]

Preparation of 3-amino-N-[3,5-dichloro-4-(1-methyl-1H-pyrazol-5-yl)-2-thienyl]-2-(phenylmethyl)propanamide The title compound was prepared as an orange solid according to Example 1, except substituting 3-({[(1,1-dimethylethyl)oxy]carbonyl}amino)-2-(phenylmethyl)propanoic acid (360 mg, 1.290 mmol)[prepared in Preparation 3] for 3-({[(1,1-dimethylethyl)oxy]carbonyl}amino)-2-phenylpropanoic acid (342 mg, 1.290 mmol):

LCMS (ES) m/e 409, 411 (M, M+2)+; $^1$H NMR (400 MHz, DMSO-d$_6$) δ ppm 11.50 (br. s., 1 H) 8.11 (br. s., 3 H) 7.57 (d, J=1.77 Hz, 1 H) 7.16-7.40 (m, 5 H) 6.38 (d, J=6.82 Hz, 1 H) 3.65-3.69 (m, 3 H) 3.56-3.62 (m, 1 H) 3.08 (br. s., 1 H) 3.03 (br. s., 1 H) 2.80 (br. s., 2 H).

Example 3

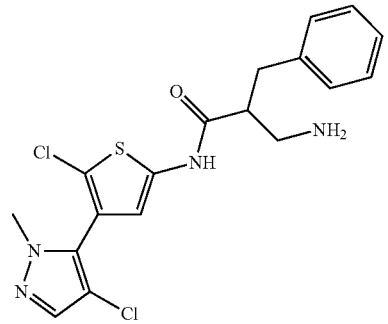 [SMILES: Cn1ncc(Cl)c1-c1cc(NC(=O)C(CN)Cc2ccccc2)sc1Cl]

Preparation of 3-amino-N-[5-chloro-4-(4-chloro-1-methyl-1H-pyrazol-5-yl)-2-thienyl]-2-(phenylmethyl)propanamide a) methyl 5-chloro-4-(1-methyl-1H-pyrazol-5-yl)-2-thiophenecarboxylate

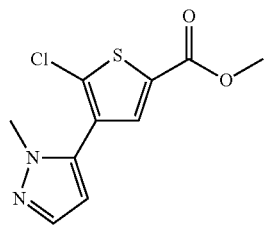

A solution of methyl 4-bromo-5-chloro-2-thiophenecarboxylate (5 g, 19.57 mmol)[prepared in Preparation 2], 1-methyl-5-(4,4,5,5-tetramethyl-1,3,2-dioxaborolan-2-yl)-1H-pyrazole (4.28 g, 20.55 mmol)[prepared in Preparation 1], potassium carbonate (10.82 g, 78 mmol) and bis(tri-t-butylphosphine)palladium(0) (0.500 g, 0.978 mmol) in 1,4-dioxane (82 ml) and water (16.31 ml) was stirred at 80° C. in a sealed tube for 2 h. The reaction mixture was partitioned between H$_2$O-DCM and the aqueous phase was washed several times with DCM. The combined organic fractions were dried over Na$_2$SO$_4$, concentrated and purified via column chromatography (silica, 25% EtOAc in hexanes) yielding methyl 5-chloro-4-(1-methyl-1H-pyrazol-5-yl)-2-thiophenecarboxylate (3.2 g, 12.47 mmol, 63.7% yield) as a white solid: LCMS m/e ES 257, 259 (M, M+2)+.

b) 5-chloro-4-(4-chloro-1-methyl-1H-pyrazol-5-yl)-2-thiophenecarboxylic acid

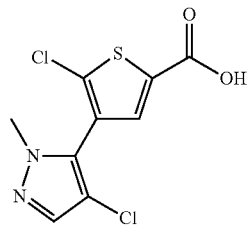 [SMILES: Cn1ncc(Cl)c1-c1cc(C(=O)O)sc1Cl]

A solution of methyl 5-chloro-4-(1-methyl-1H-pyrazol-5-yl)-2-thiophenecarboxylate (3.2 g, 12.47 mmol) and n-chlorosuccinimide (1.665 g, 12.47 mmol) in tetrahydrofuran (62.3 ml) was stirred in a sealed tube for 1 h at 70° C. 6N sodium hydroxide (41.6 ml, 249 mmol) was added in one portion and the solution stirred an additional 12 h. The reaction mixture was then partitioned between H₂O-DCM and the pH of the aqueous phase was adjusted to ~4 and washed several times with DCM. The combined organic fractions were dried over Na₂SO₄, concentrated and used directly without further purification yielding 5-chloro-4-(4-chloro-1-methyl-1H-pyrazol-5-yl)-2-thiophenecarboxylic acid (5 g, 17.86 mmol, 143% yield) as a white solid: LCMS (ES) m/e 277, 279 (M, M+2)$^+$.

c) 1,1-dimethylethyl[5-chloro-4-(4-chloro-1-methyl-1H-pyrazol-5-yl)-2-thienyl]carbamate

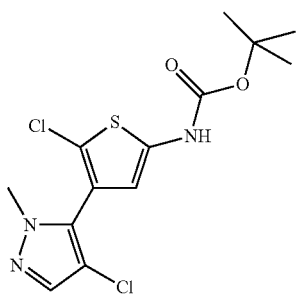 [SMILES: Cn1ncc(Cl)c1-c1cc(NC(=O)OC(C)(C)C)sc1Cl]

To a solution of 5-chloro-4-(4-chloro-1-methyl-1H-pyrazol-5-yl)-2-thiophenecarboxylic acid (2 g, 7.22 mmol) in toluene (60.1 ml) at 0° C. was added triethylamine (1.308 ml, 9.38 mmol) followed by diphenyl 2l5-1-triazen-2-yn-1-ylphosphonate (1.552 ml, 7.22 mmol). After 6 h at 25° C., the reaction solution was filtered through a plug of silica and concentrated to a brown oil. The residue was redissolved in 1,4-dioxane (60.1 ml) and tBuOH (6.90 ml, 72.2 mmol) and heated to 95° C. After 12 h, the solution was cooled and partitioned between H₂O-DCM and the aqueous phase was washed several times with DCM. The combined organic fractions were dried over Na₂SO₄, dry loaded onto silica and purified by chromatography (0-50% EtOAc in hexanes) affording 1,1-dimethylethyl[5-chloro-4-(4-chloro-1-methyl-1H-pyrazol-5-yl)-2-thienyl]carbamate (1.3 g, 3.43 mmol, 47.6% yield) as a yellow solid: LCMS (ES) m/e 348, 350 (M, M+2)$^+$.

d) [5-chloro-4-(4-chloro-1-methyl-1H-pyrazol-5-yl)-2-thienyl]amine

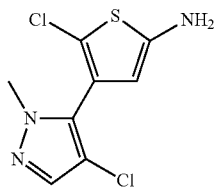

To a solution of 1,1-dimethylethyl[5-chloro-4-(4-chloro-1-methyl-1H-pyrazol-5-yl)-2-thienyl]carbamate (1.3 g, 3.73 mmol) in methanol (18.66 ml) at 25° C. was added HCl (18.66 ml, 74.7 mmol)[4M in dioxane]. After 12 h, additional HCl (18.66 ml, 74.7 mmol)[4M in dioxane] was added and the solution stirred 12 h. The reaction mixture was concentrated to a dark foam affording the HCl salt of [5-chloro-4-(4-chloro-1-methyl-1H-pyrazol-5-yl)-2-thienyl]amine (1.1 g, 99% yield): LCMS (ES) m/e 248, 250 (M, M+2)$^+$.

e) 1,1-dimethylethyl[3-{[5-chloro-4-(4-chloro-1-methyl-1H-pyrazol-5-yl)-2-thienyl]amino}-3-oxo-2-(phenylmethyl)propyl]carbamate

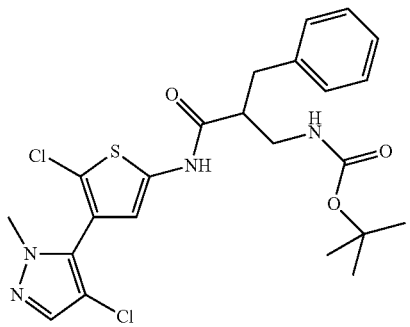 [SMILES: Cn1ncc(Cl)c1-c1cc(NC(=O)C(CNC(=O)OC(C)(C)C)Cc2ccccc2)sc1Cl]

To a solution of 3-({[(1,1-dimethylethyl)oxy]carbonyl}amino)-2-(phenylmethyl)propanoic acid (675 mg, 2.418 mmol)[prepared in Preparation 3], [5-chloro-4-(4-chloro-1-methyl-1H-pyrazol-5-yl)-2-thienyl]amine (600 mg, 2.418 mmol) and DIPEA (2.112 ml, 12.09 mmol) in dichloromethane (12.100 ml) at 25° C. was added bromo-tris-pyrrolidino-phosphonium hexafluorophosphate (1356 mg, 2.90 mmol) in one portion. After 1 h, additional DIPEA (2.112 ml, 12.09 mmol), 3-({[(1,1-dimethylethyl)oxy]carbonyl}amino)-2-(phenylmethyl)propanoic acid (675 mg, 2.418 mmol) and bromo-tris-pyrrolidino-phosphonium hexafluorophosphate (1356 mg, 2.90 mmol) were added and the solution stirred 12 h. The reaction mixture was dry loaded onto silica and purified by chromatography (0-70% EtOAc in hexanes) affording 1,1-dimethylethyl[3-{[5-chloro-4-(4-chloro-1-methyl-1H-pyrazol-5-yl)-2-thienyl]amino}-3-oxo-2-(phenylmethyl)propyl]carbamate (740 mg, 1.089 mmol, 45.1% yield) as a orange oil:

LCMS (ES) m/e 509, 511 (M, M+2)$^+$.

f) 3-amino-N-[5-chloro-4-(4-chloro-1-methyl-1H-pyrazol-5-yl)-2-thienyl]-2-(phenylmethyl)propanamide To a solution of 1,1-dimethylethyl[3-{[5-chloro-4-(4-chloro-1-methyl-1H-pyrazol-5-yl)-2-thienyl]amino}-3-oxo-2-(phenylmethyl)propyl]carbamate (740 mg, 1.453 mmol) in dichloromethane (7.263 ml) at 25° C. was added TFA (1.119 ml, 14.53 mmol) in one portion. After 30 min, the solution was dry loaded onto silica and neutralized through silica (0-20% MeOH in DCM (1% NH₄OH) affording the free base of the title compound. The free base was then dissolved in MeOH (10 mL) and treated with excess 4M HCl in dioxane (2 mL) providing the HCl salt of 3-amino-N-[5-chloro-4-(4-chloro-1-methyl-1H-pyrazol-5-yl)-2-thienyl]-2-(phenylmethyl)propanamide (426 mg, 0.908 mmol, 62.5% yield) as an orange solid: LCMS (ES) m/e 409, 411 (M, M+2)$^+$; $^1$H NMR (400 MHz, DMSO-d₆) δ ppm 12.34 (s, 1 H) 8.06 (br. s., 3 H) 7.68 (s, 1 H) 7.26-7.40 (m, 4 H) 7.24 (d, J=6.82 Hz, 1 H) 6.70 (s, 1 H) 3.94-3.96 (m, 1 H) 3.70 (s, 3 H) 3.14-3.17 (m, 1 H) 3.05 (dd, J=13.52, 6.44 Hz, 2 H) 2.85 (dd, J=14.02, 7.45 Hz, 2 H).

Example 4

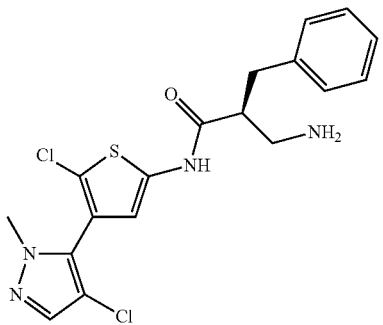 [SMILES: Cn1ncc(Cl)c1-c1cc(NC(=O)[C@H](CN)Cc2ccccc2)sc1Cl]

Preparation of (2S)-3-amino-N-[5-chloro-4-(4-chloro-1-methyl-1H-pyrazol-5-yl)-2-thienyl]-2-(phenylmethyl)propanamide The title compound was obtained through chiral resolution of racemic 3-amino-N-[5-chloro-4-(4-chloro-1-methyl-1H-pyrazol-5-yl)-2-thienyl]-2-(phenylmethyl)propanamide using a Chiralpak AD-H column (4.6×150 mm) and eluting with methanol (0.1% Isopropylamine) at a retention time of 3.1 min. The free base, as a solution in MeOH (2 mL) was treated with excess 4M HCl in dioxanes affording the HCl salt of the title compound as an orange solid: LCMS (ES) m/e 409, 411 (M, M+2)$^+$; $^1$H NMR (400 MHz, DMSO-d$_6$) δ ppm 12.34 (s, 1 H) 8.06 (br. s., 3 H) 7.68 (s, 1 H) 7.26-7.40 (m, 4 H) 7.24 (d, J=6.82 Hz, 1 H) 6.70 (s, 1 H) 3.94-3.96 (m, 1 H) 3.70 (s, 3 H) 3.14-3.17 (m, 1 H) 3.05 (dd, J=13.52, 6.44 Hz, 2 H) 2.85 (dd, J=14.02, 7.45 Hz, 2 H).

Example 5

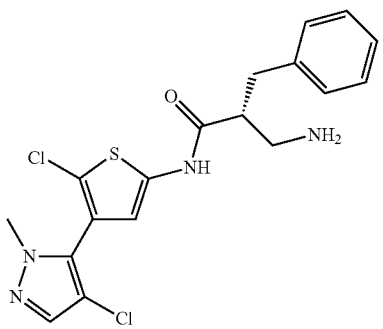 [SMILES: Cn1ncc(Cl)c1-c1cc(NC(=O)[C@@H](CN)Cc2ccccc2)sc1Cl]

Preparation of (2R)-3-amino-N-[5-chloro-4-(4-chloro-1-methyl-1H-pyrazol-5-yl)-2-thienyl]-2-(phenylmethyl)propanamide The title compound was obtained through chiral resolution of racemic 3-amino-N-[5-chloro-4-(4-chloro-1-methyl-1H-pyrazol-5-yl)-2-thienyl]-2-(phenylmethyl)propanamide using a Chiralpak AD-H column (4.6×150 mm) and eluting with methanol (0.1% Isopropylamine) at a retention time of 5.3 min. The free base, as a solution in MeOH (2 mL) was treated with excess 4M HCl in dioxanes affording the HCl salt of the title compound as an orange solid: LCMS (ES) m/e 409, 411 (M, M+2)$^+$; $^1$H NMR (400 MHz, DMSO-d$_6$) δ ppm 12.34 (s, 1 H) 8.06 (br. s., 3 H) 7.68 (s, 1 H) 7.26-7.40 (m, 4 H) 7.24 (d, J=6.82 Hz, 1 H) 6.70 (s, 1 H) 3.94-3.96 (m, 1 H) 3.70 (s, 3 H) 3.14-3.17 (m, 1 H) 3.05 (dd, J=13.52, 6.44 Hz, 2 H) 2.85 (dd, J=14.02, 7.45 Hz, 2 H).

Example 6

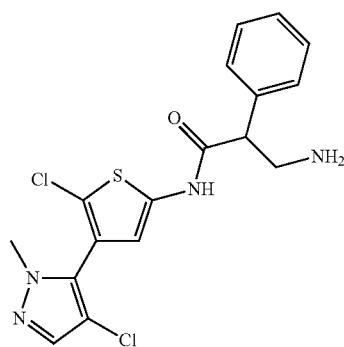 [SMILES: Cn1ncc(Cl)c1-c1cc(NC(=O)C(CN)c2ccccc2)sc1Cl]

Preparation of 3-amino-N-[5-chloro-4-(4-chloro-1-methyl-1H-pyrazol-5-yl)-2-thienyl]-2-(phenyl)propanamide The title compound was prepared as an orange solid according to Example 3, except substituting 3-({[(1,1-dimethylethyl)oxy]carbonyl}amino)-2-phenylpropanoic acid (0.559 g, 2.108 mmol) for 3-({[(1,1-dimethylethyl)oxy]carbonyl}amino)-2-(phenylmethyl)propanoic acid: LCMS (ES) m/e 395, 397 (M, M+2)$^+$; $^1$H NMR (400 MHz, DMSO-d$_6$) δ ppm 12.28 (br. s., 1 H) 8.07 (br. s., 3 H) 7.67 (s, 1 H) 7.27-7.49 (m, 5 H) 6.66 (s, 1 H) 4.19 (dd, J=9.22, 5.18 Hz, 2 H) 3.98-4.09 (m, 1H) 3.67 (s, 3 H) 3.11 (dd, J=12.13, 6.32 Hz, 1 H).

Example 7

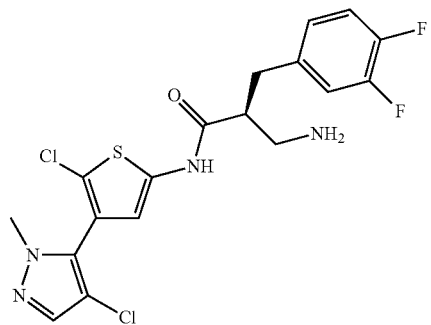 [SMILES: Cn1ncc(Cl)c1-c1cc(NC(=O)[C@H](CN)Cc2ccc(F)c(F)c2)sc1Cl]

Preparation of (2S)-3-amino-N-[5-chloro-4-(4-chloro-1-methyl-1H-pyrazol-5-yl)-2-thienyl]-2-[(3,4-difluorophenyl)methyl]propanamide a) phenylmethyl {(2S)-3-{[5-chloro-4-(4-chloro-1-methyl-1H-pyrazol-5-yl)-2-thienyl]amino}-2-[(3,4-difluorophenyl)methyl]-3-oxopropyl}carbamate

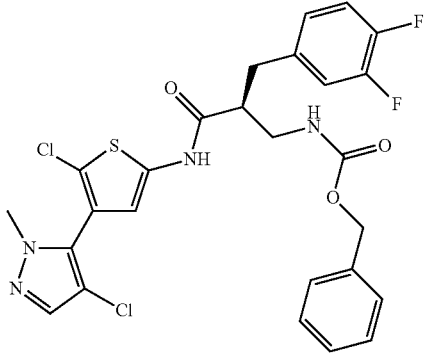 [SMILES: Cn1ncc(Cl)c1-c1cc(NC(=O)[C@H](CNC(=O)OCc2ccccc2)Cc2ccc(F)c(F)c2)sc1Cl]

Bromo-tris-pyrrolidino phosphoniumhexafluorophosphate (401 mg, 0.859 mmol) was added in one portion to a solution of (2S)-3-(3,4-difluorophenyl)-2-[({[(phenylmethyl)oxy]carbonyl}amino)methyl]propanoic acid (200 mg, 0.573 mmol)[prepared in Preparation 4] and [5-chloro-4-(4-chloro-1-methyl-1H-pyrazol-5-yl)-2-thienyl]amine-HCl (163 mg, 0.573 mmol)[prepared in Example 3] in N,N-diisopropylethylamine (0.500 ml, 2.86 mmol) and dichloromethane (7.174 ml). After 12 h, the solution was dry loaded onto silica and purified by chromatography (0-50% EtOAc in hexanes) affording phenylmethyl {(2S)-3-{[5-chloro-4-(4-chloro-1-methyl-1H-pyrazol-5-yl)-2-thienyl]amino}-2-[(3,4-difluorophenyl)methyl]-3-oxopropyl}carbamate (70 mg, 0.115 mmol, 20.05% yield) as an orange solid: LCMS (ES) m/e 579, 581 (M, M+2)+, 1H NMR (400 MHz, DMSO-d6) d ppm 11.61 (s, 1 H) 7.67 (s, 1 H) 7.53 (br. s., 1 H) 7.32 (s, 7 H) 7.03 (br. s., 1 H) 6.55 (s, 1 H) 5.01 (s, 2 H) 3.68 (s, 3 H) 3.19-3.28 (m, 2 H) 2.76-3.00 (m, 3 H).

b) (2S)-3-amino-N-[5-chloro-4-(4-chloro-1-methyl-1H-pyrazol-5-yl)-2-thienyl]-2-[(3,4-difluorophenyl)methyl]propanamide Phenylmethyl {(2S)-3-{[5-chloro-4-(4-chloro-1-methyl-1H-pyrazol-5-yl)-2-thienyl]amino}-2-[(3,4-difluorophenyl)methyl]-3-oxopropyl}carbamate (91 mg, 0.157 mmol) was dissolved in a solution of thioanisole (0.286 ml) in trifluoroacetic acid (2.855 ml). After 4 h at 25° C., the reaction mixture was dry loaded onto silica and neutralized/purified through silica chromatography (0-15% MeOH in DCM (1% NH4OH)) affording the free base of the title compound.

The free base, as a solution in MeOH (2 mL) was treated with excess 4M HCl in dioxane (1 mL) yielding the HCl salt of (2S)-3-amino-N-[5-chloro-4-(4-chloro-1-methyl-1H-pyrazol-5-yl)-2-thienyl]-2-[(3,4-difluorophenyl)methyl]propanamide (40 mg, 0.079 mmol, 50.2% yield) as a yellow solid: LCMS (ES) m/e 445, 447 (M, M+2)+, 1H NMR (400 MHz, DMSO-d6) δ ppm 12.33 (s, 1 H) 8.02 (br. s., 2 H) 7.68 (s, 1 H) 7.29-7.52 (m, 1 H) 7.40 (t, J=8.46 Hz, 1 H) 7.13 (br. s., 1 H) 6.69 (s, 1 H) 3.67 (s, 3 H) 3.48 (dd, J=11.62, 4.29 Hz, 1 H) 3.12-3.18 (m, 1 H) 3.01 (d, J=6.32 Hz, 1 H) 2.75-2.89 (d, J=7.33 Hz, 2 H).

Example 8

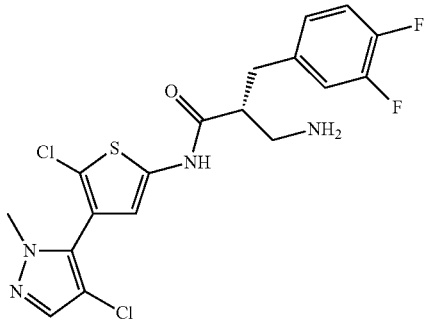 [SMILES: Cn1ncc(Cl)c1-c1cc(NC(=O)[C@@H](CN)Cc2ccc(F)c(F)c2)sc1Cl]

Preparation of (2R)-3-amino-N-[5-chloro-4-(4-chloro-1-methyl-1H-pyrazol-5-yl)-2-thienyl]-2-[(3,4-difluorophenyl)methyl]propanamide The title compound was prepared as a yellow solid according to Example 7, except substituting (2R)-3-(3,4-difluorophenyl)-2-[({[(phenylmethyl)oxy]carbonyl}amino)methyl]propanoic acid (260 mg, 0.744 mmol) for (2S)-3-(3,4-difluorophenyl)-2-[({[(phenylmethyl)oxy]carbonyl}amino)methyl]propanoic acid[prepared in Preparation 4]: LCMS (ES) m/e 445, 447 (M, M+2)+, 1H NMR (400 MHz, DMSO-d6) δ ppm 12.33 (s, 1 H) 8.02 (br. s., 2 H) 7.68 (s, 1 H) 7.29-7.52 (m, 1 H) 7.40 (t, J=8.46 Hz, 1 H) 7.13 (br. s., 1 H) 6.69 (s, 1 H) 3.67 (s, 3 H) 3.48 (dd, J=11.62, 4.29 Hz, 1 H) 3.12-3.18 (m, 1 H) 3.01 (d, J=6.32 Hz, 1 H) 2.75-2.89 (d, J=7.33 Hz, 2 H).

Example 9

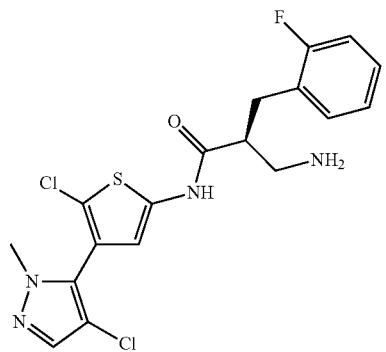 [SMILES: Cn1ncc(Cl)c1-c1cc(NC(=O)[C@H](CN)Cc2ccccc2F)sc1Cl]

Preparation of (2S)-3-amino-N-[5-chloro-4-(4-chloro-1-methyl-1H-pyrazol-5-yl)-2-thienyl]-2-[(2-fluorophenyl)methyl]propanamide The title compound was prepared as a yellow solid according to Example 7, except substituting (2S)-3-(2-fluorophenyl)-2-[({[(phenylmethyl)oxy]carbonyl}amino)methyl]propanoic acid (220 mg, 0.664 mmol) for (2S)-3-(3,4-difluorophenyl)-2-[({[(phenylmethyl)oxy]carbonyl}amino)methyl]propanoic acid[prepared in Preparation 4]: LCMS (ES) m/e 427, 429 (M, M+2)+, 1H NMR (400 MHz, DMSO-d6) δ ppm 12.00 (br. s., 1 H) 7.92 (br. s., 3 H) 7.69 (s, 1 H) 7.32

(t, J=7.07 Hz, 2 H) 7.16 (t, J=7.45 Hz, 2 H) 6.65 (s, 1 H) 3.70 (s, 3 H) 3.15 (br. s., 2 H) 2.99 (br. s., 3 H).

Example 10

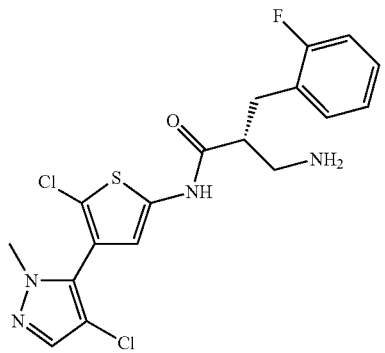 [SMILES: Cn1ncc(Cl)c1-c1cc(NC(=O)[C@@H](CN)Cc2ccccc2F)sc1Cl]

Preparation of (2R)-3-amino-N-[5-chloro-4-(4-chloro-1-methyl-1H-pyrazol-5-yl)-2-thienyl]-2-[(2-fluorophenyl)methyl]propanamide The title compound was prepared as a yellow solid according to Example 7, except substituting (2R)-3-(2-fluorophenyl)-2-[({[(phenylmethyl)oxy]carbonyl}amino)methyl]propanoic acid (240 mg, 0.724 mmol) for (2S)-3-(3,4-difluorophenyl)-2-[({[(phenylmethyl)oxy]carbonyl}amino)methyl]propanoic acid[prepared in Preparation 4]: LCMS (ES) m/e 427, 429 (M, M+2)+, $^1$H NMR (400 MHz, DMSO-$d_6$) δ ppm 12.00 (br. s., 1 H) 7.92 (br. s., 3 H) 7.69 (s, 1 H) 7.32 (t, J=7.07 Hz, 2 H) 7.16 (t, J=7.45 Hz, 2 H) 6.65 (s, 1 H) 3.70 (s, 3 H) 3.15 (br. s., 2 H) 2.99 (br. s., 3 H).

Example 11

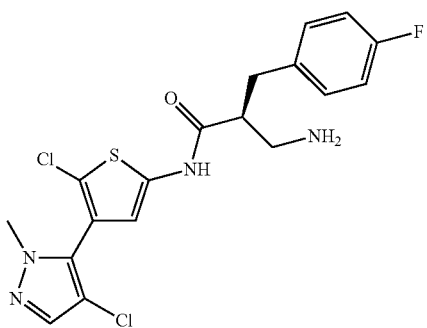 [SMILES: Cn1ncc(Cl)c1-c1cc(NC(=O)[C@H](CN)Cc2ccc(F)cc2)sc1Cl]

Preparation of (2S)-3-amino-N-[5-chloro-4-(4-chloro-1-methyl-1H-pyrazol-5-yl)-2-thienyl]-2-[(4-fluorophenyl)methyl]propanamide The title compound was prepared as a yellow solid according to Example 7, except substituting (2S)-3-(4-fluorophenyl)-2-[({[(phenylmethyl)oxy]carbonyl}amino)methyl]propanoic acid (250 mg, 0.755 mmol) for (2S)-3-(3,4-difluorophenyl)-2-[({[(phenylmethyl)oxy]carbonyl}amino)methyl]propanoic acid[prepared in Preparation 4]: LCMS (ES) m/e 427, 429 (M, M+2)+, $^1$H NMR (400 MHz, DMSO-$d_6$) δ ppm 12.18 (s, 1 H) 7.95 (br. s., 3 H) 7.69 (s, 1 H) 7.31 (dd, J=8.46, 5.68 Hz, 2 H) 7.16 (t, J=8.84 Hz, 2 H) 6.68 (s, 1 H) 3.70 (s, 3 H) 3.08-3.21 (m, 2 H) 3.03 (d, J=13.64 Hz, 1 H) 2.86 (d, J=13.89 Hz, 1 H) 2.83 (br. s., 1 H).

Example 12

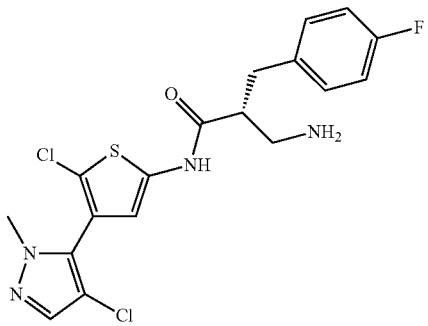 [SMILES: Cn1ncc(Cl)c1-c1cc(NC(=O)[C@@H](CN)Cc2ccc(F)cc2)sc1Cl]

Preparation of (2R)-3-amino-N-[5-chloro-4-(4-chloro-1-methyl-1H-pyrazol-5-yl)-2-thienyl]-2-[(4-fluorophenyl)methyl]propanamide The title compound was prepared as a yellow solid according to Example 7, except substituting (2R)-3-(4-fluorophenyl)-2-[({[(phenylmethyl)oxy]carbonyl}amino)methyl]propanoic acid (250 mg, 0.755 mmol) for (2S)-3-(3,4-difluorophenyl)-2-[({[(phenylmethyl)oxy]carbonyl}amino)methyl]propanoic acid[prepared in Preparation 4]: LCMS (ES) m/e 427, 429 (M, M+2)+, 1H NMR (400 MHz, DMSO-$d_6$) δ ppm 12.18 (s, 1 H) 7.95 (br. s., 3 H) 7.69 (s, 1 H) 7.31 (dd, J=8.46, 5.68 Hz, 2 H) 7.16 (t, J=8.84 Hz, 2 H) 6.68 (s, 1 H) 3.70 (s, 3 H) 3.08-3.21 (m, 2 H) 3.03 (d, J=13.64 Hz, 1 H) 2.86 (d, J=13.89 Hz, 1 H) 2.83 (br. s., 1 H).

Example 13

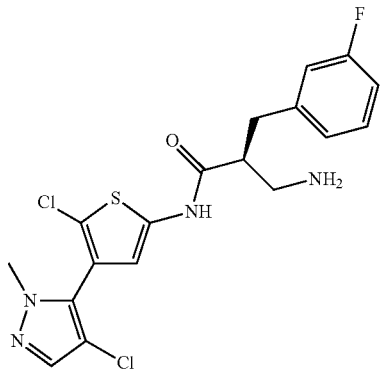 [SMILES: Cn1ncc(Cl)c1-c1cc(NC(=O)[C@H](CN)Cc2cccc(F)c2)sc1Cl]

Preparation of (2S)-3-amino-N-[5-chloro-4-(4-chloro-1-methyl-1H-pyrazol-5-yl)-2-thienyl]-2-[(3-fluorophenyl)methyl]propanamide The title compound was prepared as a yellow solid according to Example 7, except substituting (2S)-3-(3-fluorophenyl)-2-[({[(phenylmethyl)oxy]carbonyl}amino)methyl]propanoic acid (0.50 g, 1.51 mmol) for (2S)-3-(3,4-difluorophenyl)-2-[({[(phenylmethyl)oxy]carbonyl}amino)methyl]propanoic acid[prepared in Preparation 4]: LCMS (ES) m/e 427, 429 (M, M+2)+, 1H NMR (400 MHz, DMSO-d$_6$) δ ppm 12.54 (s, 1H) 8.15 (br. s., 3H) 7.68 (s, 1H) 7.35 (dd, J=8.5, 5.7 Hz, 2H) 7.16 (d, J=10.0 Hz, 1H), 7.12 (d, J=7.6, 1H), 7.06 (m, 1H), 6.72 (s, 1H) 4.07 (br s, 3H), 3.70 (s, 3 H), 3.48 (m, 1H), 3.25 (m, 1H) 3.03-3.15 (m, 2H), 2.89 (m, 1H) 2.78 (m, 1H).

Example 14

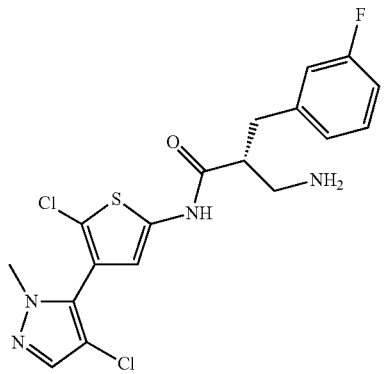 [SMILES: Cn1ncc(Cl)c1-c1cc(NC(=O)[C@@H](CN)Cc2cccc(F)c2)sc1Cl]

Preparation of (2R)-3-amino-N-[5-chloro-4-(4-chloro-1-methyl-1H-pyrazol-5-yl)-2-thienyl]-2-[(3-fluorophenyl)methyl]propanamide The title compound was prepared as a yellow solid according to Example 7, except substituting (2R)-3-(3-fluorophenyl)-2[({[(phenylmethyl)oxy]carbonyl}amino)methyl]propanoic acid (0.60 g, 1.81 mmol) for (2S)-3-(3,4-difluorophenyl)-2-[({[(phenylmethyl)oxy]carbonyl}amino)methyl]propanoic acid[prepared in Preparation 4]: LCMS (ES) m/e 427, 429 (M, M+2)+, 1H NMR (400 MHz, DMSO-d$_6$) δ ppm 12.54 (s, 1H) 8.15 (br. s., 3H) 7.68 (s, 1H) 7.35 (dd, J=8.5, 5.7 Hz, 2H) 7.16 (d, J=10.0 Hz, 1H), 7.12 (d, J=7.6, 1H), 7.06 (m, 1H), 6.72 (s, 1H) 4.07 (br s, 3H), 3.70 (s, 3 H), 3.48 (m, 1H), 3.25 (m, 1H) 3.03-3.15 (m, 2H), 2.89 (m, 1H) 2.78 (m, 1H).

Example 15

Capsule Composition

An oral dosage form for administering the present invention is produced by filing a standard two piece hard gelatin capsule with the ingredients in the proportions shown in Table I, below.

TABLE I

| INGREDIENTS | AMOUNTS |
|---|---|
| N-{(1S)-2-amino-1-[(3-fluorophenyl)methyl]ethyl}-1-(1-methyl-1H-pyrazol-5-yl)-1H-pyrrole-3-carboxamide (Compound of Example 1) | 25 mg |
| Lactose | 55 mg |
| Talc | 16 mg |
| Magnesium Stearate | 4 mg |

Example 16

Injectable Parenteral Composition

An injectable form for administering the present invention is produced by stirring 1.5% by weight of (2S)-3-amino-N-[5-chloro-4-(4-chloro-1-methyl-1H-pyrazol-5-yl)-2-thienyl]-2-[(2-fluorophenyl)methyl]propanamide (Compound of Example 9) in 10% by volume propylene glycol in water.

Example 17

Tablet Composition

The sucrose, calcium sulfate dihydrate and an Akt inhibitor as shown in Table II below, are mixed and granulated in the proportions shown with a 10% gelatin solution. The wet granules are screened, dried, mixed with the starch, talc and stearic acid;, screened and compressed into a tablet.

TABLE II

| INGREDIENTS | AMOUNTS |
|---|---|
| (2S)-3-amino-N-[5-chloro-4-(4-chloro-1-methyl-1H-pyrazol-5-yl)-2-thienyl]-2-[(3-fluorophenyl)methyl]propanamide (Compound of Example 13) | 20 mg |
| calcium sulfate dihydrate | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A compound of Formula (I):

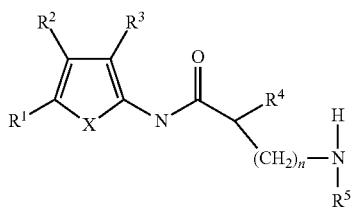

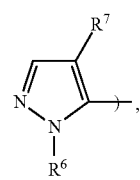

wherein:

$R^1$ and $R^2$ are independently selected from: hydrogen, halogen and $C_{1-4}$alkyl, where $R^6$ is $C_{1-4}$alkyl and $R^7$ is selected from hydrogen, $C_{1-4}$alkyl and halogen;

$R^3$ is selected from: hydrogen, halogen and $C_{1-4}$alkyl;

$R^4$ is selected from $(CH_2)_m$aryl wherein the aryl is either unsubstituted or substituted, where m is 0 to 2;

$R^5$ is selected from hydrogen and $C_{1-4}$alkyl;

X is selected from O and S; and n is 0 to 2;

provided that one and only one of $R^1$ and $R^2$ is

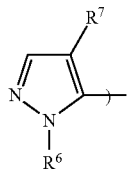

and further
provided that at least one of $R^1$, $R^2$ and $R^3$ is hydrogen;
or a salt thereof including a pharmaceutically acceptable salt thereof.

2. A compound of Formula (I) as described in claim 1, having the following Formula (II):

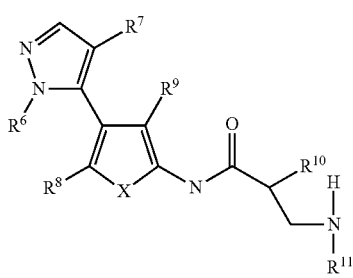

(II)

wherein:
$R^8$ and $R^9$ are independently selected from: hydrogen, halogen, and $C_{1-4}$alkyl;
$R^6$ is $C_{1-4}$alkyl;
$R^7$ is selected from hydrogen, $C_{1-4}$alkyl and halogen;
$R^{10}$ is selected from: —$(CH_2)_m C_5$-$C_{12}$aryl wherein the aryl is either unsubstituted or substituted,
where m is 0 to 2;
$R^{11}$ is selected from hydrogen and $C_{1-4}$alkyl;
X is selected from O and S; and
provided that at least one of $R^8$ and $R^9$ is hydrogen;
or a salt thereof including a pharmaceutically acceptable salt thereof.

3. A compound of Formula (I) as described in claim 1, having the following Formula (III):

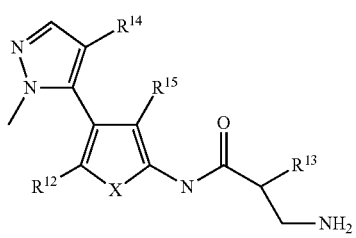

(III)

wherein:
$R^{12}$ and $R^{15}$ are independently selected from: hydrogen, halogen, and $C_{1-4}$alkyl;
$R^{13}$ is selected from: —$(CH_2)_m$phenyl wherein the phenyl is either unsubstituted or substituted,
where m is 0 to 2;
$R^{14}$ is selected from hydrogen, $C_{1-4}$alkyl and halogen;
provided that at least one of $R^{12}$ and $R^{15}$ is hydrogen;

X is selected from O and S; and
or a salt thereof including a pharmaceutically acceptable salt thereof.

4. A compound of claim 1 selected from:
3-amino-N-[5-chloro-4-(4-chloro-1-methyl-1H-pyrazol-5-yl)-2-thienyl]-2-phenylpropanamide;
3-amino-N-[5-chloro-4-(4-chloro-1-methyl-1 H-pyrazol-5-yl)-2-thienyl]-2-(phenylmethyl)propanamide;
(2S)-3-amino-N-[5-chloro-4-(4-chloro-1 -methyl-1 H-pyrazol-5-yl)-2-thienyl]-2-(phenylmethyl)propanamide;
(2R)-3-amino-N-[5-chloro-4-(4-chloro-1-methyl-1H-pyrazol-5-yl)-2-thienyl]-2-(phenylmethyl)propanamide;
3-amino-N-[3,5-chloro-4-(1 -methyl-1 H-pyrazol-5-yl-2-thienyl]-2-phenylpropanamide;
3-amino-N-[3,5-dichloro-4-(1-methyl-1H-pyrazol-5-y0-2-thienyl]-2-(phenylmethyl)propanamide;
(2S)-3-amino-N-[5-chloro-4-(4-chloro-1 -methyl-1 H-pyrazol-5-yl)-2-thienyl]-2-[(3,4-difluorophenyl)methyl]propanamide;
(2R)-3-amino-N-[5-chloro-4-(4-chloro-1 -methyl-1 H-pyrazol-5-yl)-2-thienyl]-2-[(3,4-difluorophenyl)methyl]propanamide;
(2S)-3-amino-N-[5-chloro-4-(4-chloro-1 -methyl-1 H-pyrazol-5-yl)-2-th ienyl]-2-[(2-fluorophenyl)methyl]propanamide;
(2R)-3-amino-N-[5-chloro-4-(4-chloro-1-methyl-1H-pyrazol-5-yl)-2-thienyl]-2-[(2-fluorophenyl)methyl]propanamide;
(2S)-3-amino-N-[5-chloro-4-(4-chloro-1 -methyl-1 H-pyrazol-5-yl)-2-thienyl]-2-[(4-fluorophenyl)methyl]propanamide;
(2R)-3-amino-N-[5-chloro-4-(4-chloro-1 -methyl-1 H-pyrazol-5-yl)-2-thienyl]-2-[(4-fluorophenypmethyl]propanamide;
(2S)-3-amino-N-[5-chloro-4-(4-chloro-1-methyl-1 H-pyrazol-5-yl)-2-thienyl]-2-[(3-fluorophenyOrnethyl]propanamide; and
(2R)-3-amino-N-[5-chloro-4-(4-chloro-1 -methyl-1 H-pyrazol-5-yl)-2-thienyl]-2-[(3-fluorophenyl)methyl]propanamide;
or a salt thereof including a pharmaceutically acceptable salt thereof.

5. A pharmaceutical composition comprising a compound according to claim 1, or a pharmaceutically acceptable salt thereof and a pharmaceutically acceptable carrier.

6. A process for preparing a pharmaceutical composition containing a pharmaceutically acceptable carrier or diluent and an effective amount of a compound of Formula (I) as described in claim 1 or a pharmaceutically acceptable salt thereof, which process comprises bringing the compound of Formula (I) and/or a pharmaceutically acceptable salt thereof into association with a pharmaceutically acceptable carrier or diluent.

7. A method of treating or lessening the severity of a disease or condition selected from: cancer, in a mammal in need thereof, which comprises administering to such mammal a therapeutically effective amount of a compound of Formula I, as described in claim 1 and/or a pharmaceutically acceptable salt thereof.

8. The method of claim 7 wherein the mammal is a human.

9. A method of treating or lessening the severity of a disease or condition selected from: cancer, in a mammal in need thereof, which comprises administering to such mammal a therapeutically effective amount of a compound of Formula (III), as described in claim 3 and/or a pharmaceutically acceptable salt thereof.

10. The method of claim 9 wherein the mammal is a human.

11. The method according to claim 7 wherein said cancer is selected from:
brain (gliomas), glioblastomas, Bannayan-Zonana syndrome, Cowden disease, Lhermitte-Duclos disease, breast, colon, head and neck, kidney, lung, liver, melanoma, ovarian, pancreatic, prostate, sarcoma and thyroid.

12. The method according to claim 9 wherein: said cancer is selected from brain (gliomas), glioblastomas, Bannayan-Zonana syndrome, Cowden disease, Lhermitte-Duclos disease, breast, colon, head and neck, kidney, lung, liver, melanoma, ovarian, pancreatic, prostate, sarcoma and thyroid.

13. The method of inhibiting Akt activity in a mammal in need thereof, which comprises administering to such mammal a therapeutically effective amount of a compound of Formula I, as described in claim 1 and/or a pharmaceutically acceptable salt thereof.

14. The method of claim 13 wherein the mammal is a human.

15. A method of treating cancer in a mammal in need thereof, which comprises: administering to such mammal a therapeutically effective amount of
a) a compound of Formula (I), as described in claim 1 and/or a pharmaceutically acceptable salt thereof; and
b) at least one anti-neoplastic agent.

16. The method claim 15, wherein the at least one anti-neoplastic agent is selected from the group consisting essentially of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors; non-receptor tyrosine kinase angiogenesis inhibitors; immunotherapeutic agents; proapoptotic agents; and cell cycle signaling inhibitors.

17. The method according to claim 7 wherein said cancer is selected from:
brain (gliomas), glioblastomas, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

18. The method of claim 17 wherein the mammal is a human.

* * * * *

SEQUENCE LISTING

<160> NUMBER OF SEQ ID NOS: 5

<210> SEQ ID NO 1
<211> LENGTH: 14
<212> TYPE: PRT
<213> ORGANISM: Atificial Sequence
<220> FEATURE:
<223> OTHER INFORMATION: Biotinylated synthetic peptide onto which the transfer of the gamma-phosphate from ATP is measured.

```
<400> SEQUENCE: 1

Ala Arg Lys Arg Glu Arg Ala Tyr Ser Phe Gly His His Ala
 1               5                  10

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
tatataggat ccatgagcga cgtggc                                          26

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
aaatttctcg agtcaggccg tgctgctgg                                       29

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
acctggcggc cacgctactt cctcc                                           25

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
ctcgagcatg caactagagg gcc                                             23
```